(12) United States Patent
Chiang et al.

(10) Patent No.: US 8,673,576 B2
(45) Date of Patent: Mar. 18, 2014

(54) MULTI-WAVELENGTH ANALYSES OF SOL-PARTICLE SPECIFIC BINDING ASSAYS

(75) Inventors: Vincent Chiang, San Ramon, CA (US); Rajesh K. Mehra, Hayward, CA (US)

(73) Assignee: Abaxis, Inc., Union City, CA (US)

( * ) Notice: Subject to any disclaimer, the term of this patent is extended or adjusted under 35 U.S.C. 154(b) by 0 days.

(21) Appl. No.: 13/424,217

(22) Filed: Mar. 19, 2012

(65) Prior Publication Data

US 2012/0252005 A1 Oct. 4, 2012

Related U.S. Application Data

(62) Division of application No. 12/406,906, filed on Mar. 18, 2009, now Pat. No. 8,137,920.

(60) Provisional application No. 61/038,324, filed on Mar. 20, 2008, provisional application No. 61/098,417, filed on Sep. 19, 2008.

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

U.S. PATENT DOCUMENTS

| | | | |
|---|---|---|---|
| 4,714,672 | A | 12/1987 | Rokugawa et al. |
| 5,093,271 | A | 3/1992 | Yamamoto |
| 6,514,770 | B1 | 2/2003 | Sorin |
| 6,699,724 | B1 | 3/2004 | West et al. |
| 2005/0130324 | A1 | 6/2005 | West et al. |
| 2007/0015141 | A1 | 1/2007 | Ito et al. |
| 2007/0117151 | A1 | 5/2007 | Frederix et al. |
| 2010/0266585 | A1 * | 10/2010 | Qian et al. ................ 424/133.1 |

FOREIGN PATENT DOCUMENTS

| | | |
|---|---|---|
| EP | 0269526 A2 | 6/1988 |
| EP | 0278149 A2 | 8/1988 |
| JP | H06-94719 A | 4/1994 |

OTHER PUBLICATIONS

Huang et al. (J. Am. Chem Soc. 2006 vol. 128, 2115-2120).*
Zhang et al., "Synthesis of PVP-stabilized ruthenium colloids with low boiling point alcohols," Journal of Colloid and Interface Science, vol. 313: 503-510, 2007.
Gao et al., "Determination of human complement factor C4 using resonance light-scattering technique with sodium dodecylbenzene sulphonate probe," Spectrochimica Acta Part A, vol. 64: 430-434, 2006.
Pilch, European Supplemental Search Report for European Application No. 09721836, mailed Mar. 1, 2011.
International Search Report and Written Opinion, PCT/US2009/037553, mailed Oct. 23, 2009.
Englebienne et al., "Rapid homogeneous immunoassay for human ferritin in the Cobas Mira using colloidal gold as the reporter reagent," Clinical Chem., vol. 46:2000-2003, 2000.
Jiang et al., "Gold-labeled nanoparticle-based immunoresonance scattering spectral assay for trace apolipoprotein AI and apolipoprotein B," Clinical Chem., vol. 52:1389-1394, 2006.
Alekseeva et al., "Preparation and optical scattering characterization of gold nanorods and their application to a dot-immunogold assay," Applied Optics, vol. 44:6285-6295, 2005.

* cited by examiner

*Primary Examiner* — Jacob Cheu
(74) *Attorney, Agent, or Firm* — Cooley LLP

(57) ABSTRACT

The present invention discloses methods for detecting the presence of a complex between a first reagent and a second reagent in solution. In particular, the invention provides methods for qualitative or quantitative detection of an analyte or its specific binding partner in complex biological samples. The invention further discloses algorithms using summary rate changes at selected wavelengths in the absorbance spectra of colloidal metal-labeled analytes or specific binding partners to identify intermolecular interactions between the analyte and its binding partner.

37 Claims, 28 Drawing Sheets

Figure 2. Net Absorbance Spectra Comparison
Dilute Cobas Resulted Solutions 1/5X; Pathlength= 1cm Figure 5 07/27/07 Study: Comparison Between Negative and Positive Samples - Sum of First Rates
20 Negative, 10 Single Worm and 13 High Worms Canine Serum in Duplicate Figure 8 07/16/07 Study: Reaction Spectra Post Lyophilization - Trehalose
Sample=1/25X diluted FSU High Pool in Negative Pool
R1 Cut 2 Lot 060107

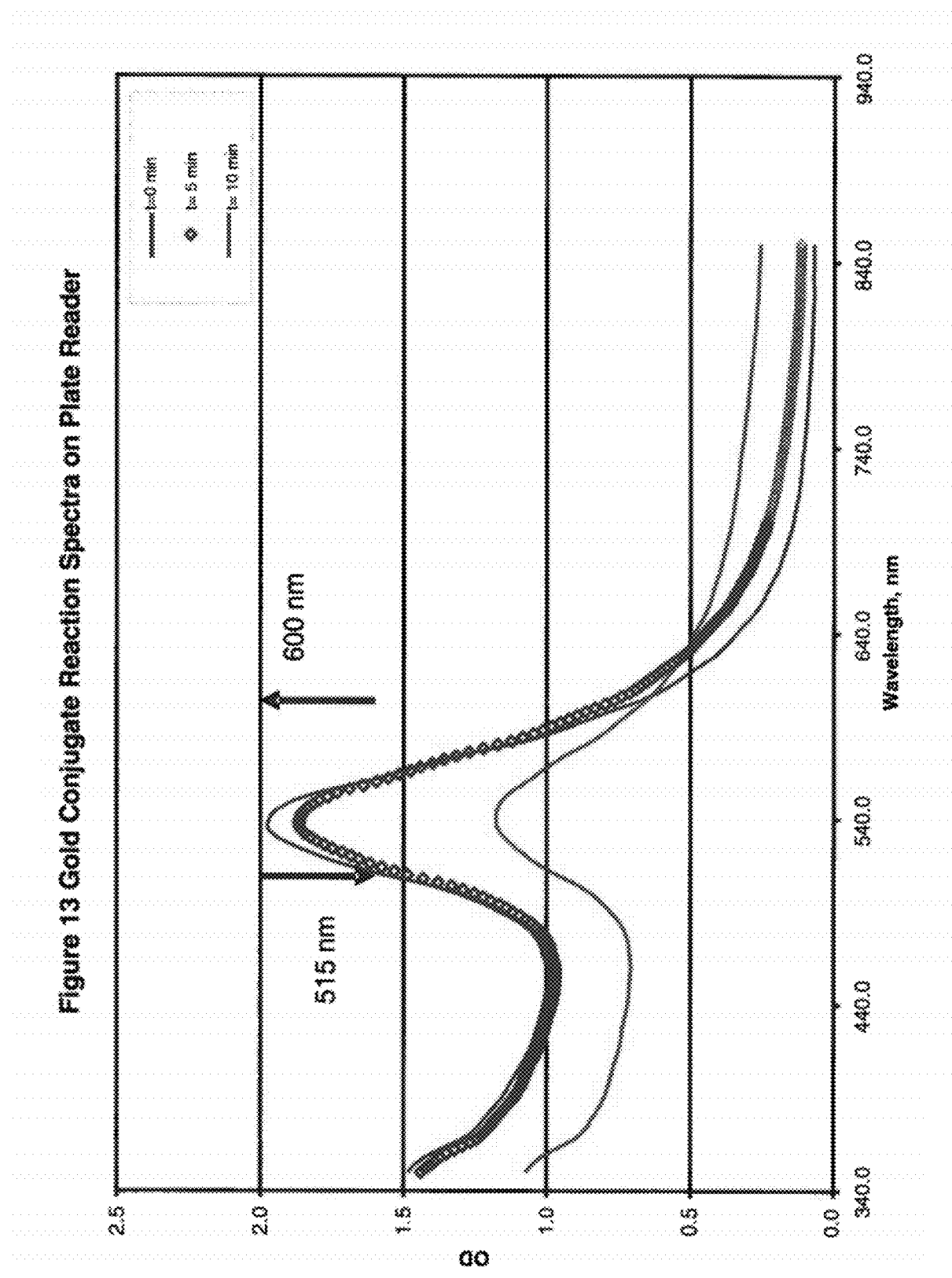

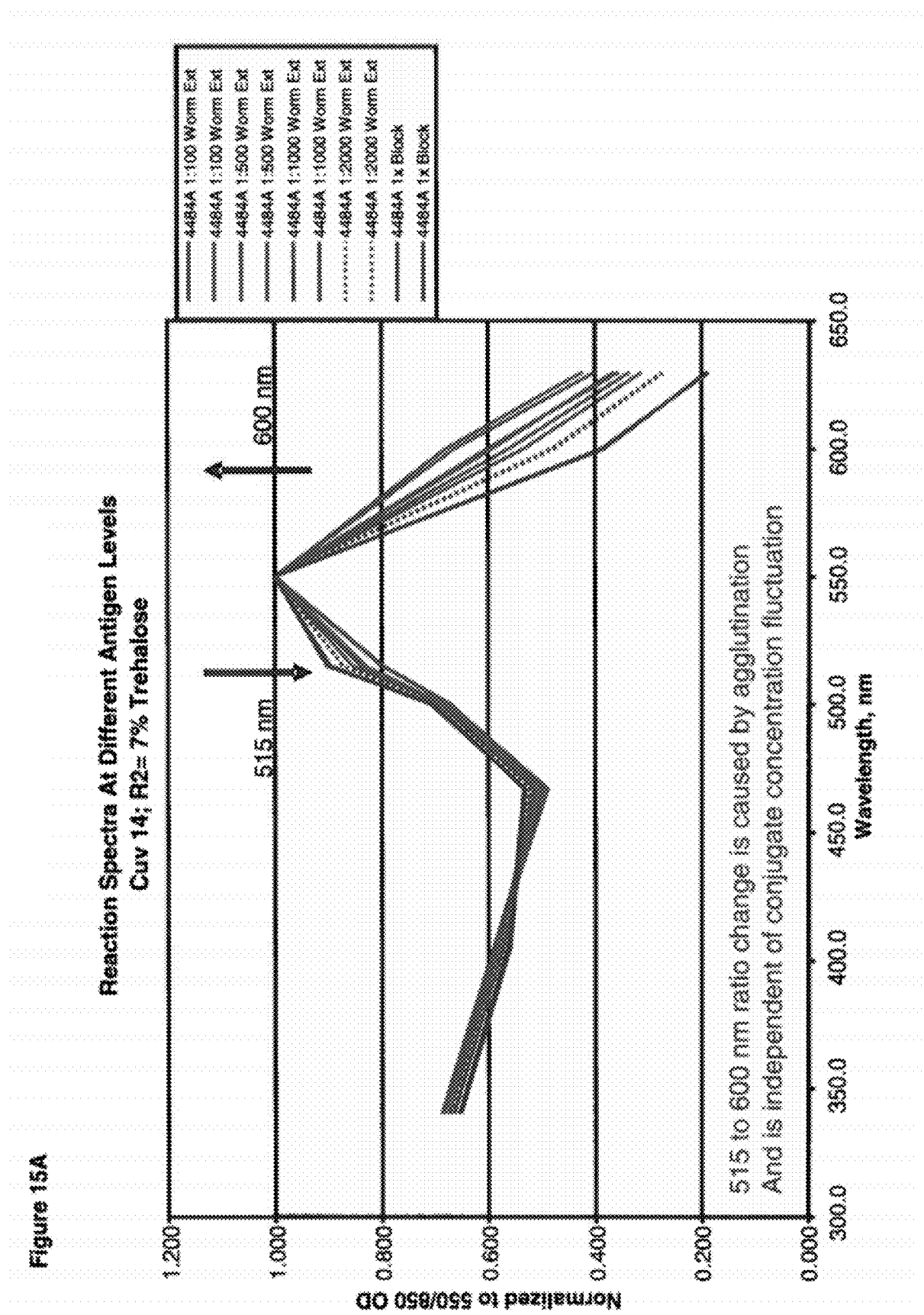

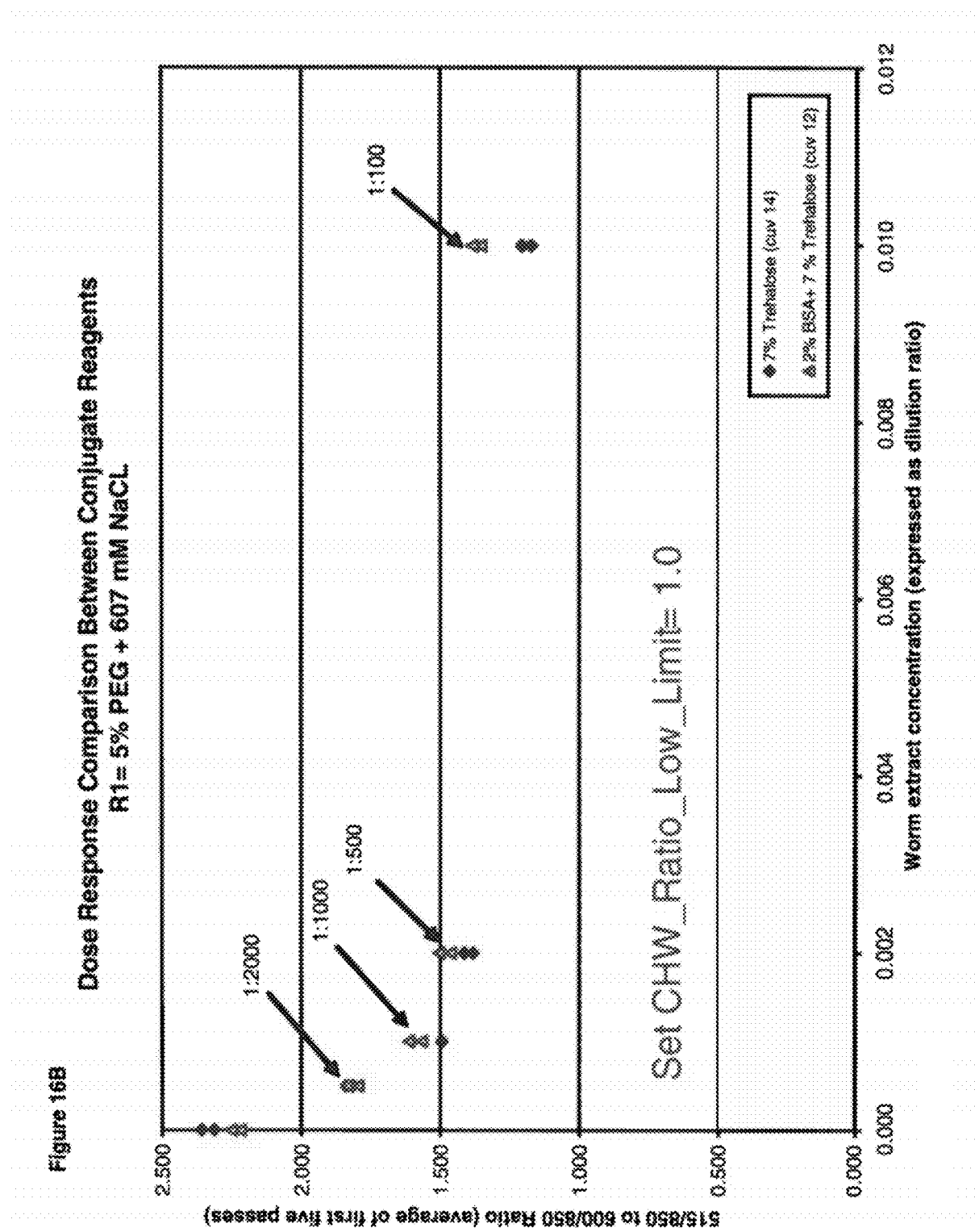

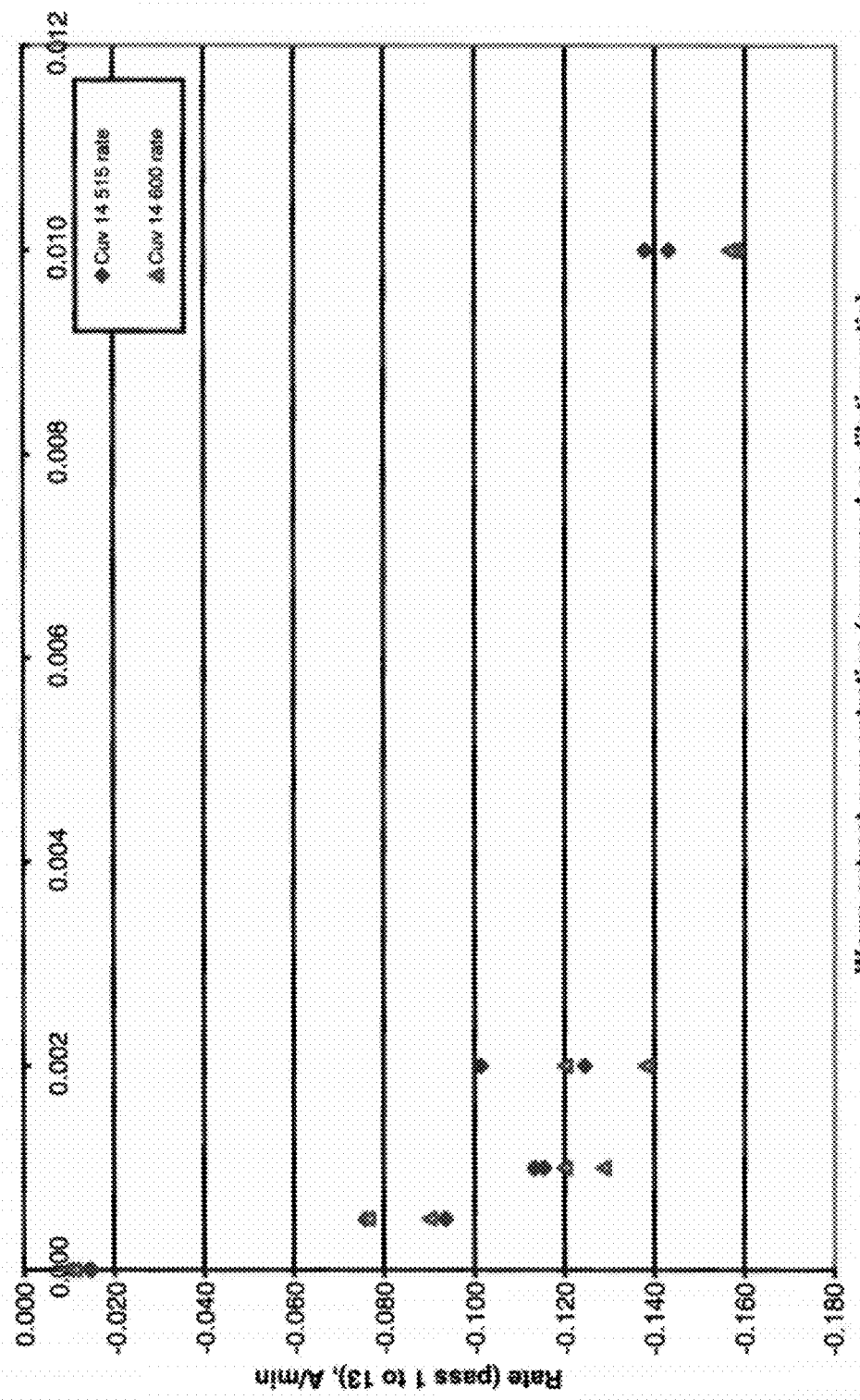

MULTI-WAVELENGTH ANALYSES OF SOL-PARTICLE SPECIFIC BINDING ASSAYS

CROSS-REFERENCE TO RELATED APPLICATIONS

This application is a divisional of U.S. application Ser. No. 12/406,906, filed Mar. 18, 2009 now U.S. Pat. No. 8,137,920, which claims priority to U.S. Patent Application Ser. No. 61/038,324, entitled "Multi-Wavelength Analyses Of Sol-Particle Specific Binding Assays", filed Mar. 20, 2008; and U.S. Patent Application Ser. No. 61/098,417, entitled "Multi-Wavelength Analyses Of Sol-Particle Specific Binding Assays", filed Sep. 19, 2008. The content of these applications are herein incorporated by reference in their entirety for all purposes.

BACKGROUND OF THE INVENTION

Accurate detection of analytes in solutions, particularly biological fluids, is critical in several fields, including medical diagnostics, veterinary diagnostics, and food and drug safety. The innate turbidity of complex biological samples, such as blood, plasma, serum, urine, and bile, has made it difficult to develop reliable assays and devices for multiple analytes. Matrix-related interference as well as scattering of light by biocolloids hamper sensitive determinations of analytes where measurements are primarily restricted to turbidity.

Several existing assay methods for detection of analytes involve the use of antibody-antigen interactions (e.g. immunoassays). These assays usually involve tagging of an antibody with radioactive material (radioimmunoassays), conjugating the antibody to an enzyme (enzyme-linked immunosorbent assay or ELISA), or coloring the antibody using colorized latex or colored metallic nanoparticles. The detection of the antibody-antigen complex then occurs by determining the presence of the label (e.g. detecting radioactivity, measuring activity of the linked enzyme, or observing a color change). These assays have one or more of the following disadvantages: (1) entail time consuming multiple analysis steps, (2) require complicated, expensive machinery for readouts, (3) are limited to detection of single analytes, and (4) are limited to qualitative analyses. Thus, there is a need for additional methods to detect one or more analytes in a biological solution.

A colloidal gold test was used to study cerebrospinal pathology and liver dysfunction in 1912. Surface plasmon resonance (SPR) is a well known phenomenon occurring in metallic nanoparticle surfaces. The phenomenon describes a graded reduction in the intensity of the reflected light due to the molecular thickness of the metal surfaces when incident light strikes the surface at a certain angle.

Localized surface plasmon resonance (LSPR) is observed in mono-dispersed nanoparticles. The collective oscillations of their conduction electrons result in wavelength selective absorption and scattering of the incident radiation. The drawback of using LSPR for biological samples has always been interference due to non-specific reaction. Therefore, it would be desirable to develop a method for detecting analytes in biological solutions that utilizes the exquisite sensitivity of LSPR, but minimizes the interference from non-specific interactions.

SUMMARY OF THE INVENTION

The present invention provides qualitative and quantitative methods for detecting an analyte or its specific binding partner in solutions, particularly biological samples. The spectroscopic methods disclosed utilize changes in the spectra of colloidal metal labeled analytes or those of the specific binding partners to determine the presence and/or quantity of an analyte. The invention further provides algorithms that employ summary rate changes in selected wavelengths to identify intermolecular interactions between an analyte and its specific binding partner.

Using nanoparticle immunoassays, the inventors of the present invention have surprisingly discovered that measurements of rates of changes at one or more wavelengths, and optionally their further numerical manipulation by an algorithm, allows for the minimization of nonspecific interference, thus substantially improving the sensitivity of such methods.

The methods of the present invention provide accurate measurement of analytes in complex biological media and can be adapted to analyze multiple analytes simultaneously using multiple measurements from multiple reaction containers each tailored for the detection of distinct analytes. Alternatively, multiple analytes can be measured simultaneously by monitoring absorbance values at several wavelengths and time points.

The present invention encompasses methods for determining the presence or absence of a complex of a first reagent and a second reagent in a mixture. In one embodiment, the method comprises determining a reaction rate change corresponding to a wavelength within an absorbance wavelength region upon mixing the first reagent with the second reagent, wherein the reaction rate change is indicative of the presence or absence of the complex of the first reagent and the second reagent. The reaction rate change may be positive or negative.

In another embodiment, the method comprises determining a first reaction rate change at a first wavelength and a second reaction rate change at a second wavelength, wherein the first wavelength and the second wavelength are within the absorbance wavelength region and wherein the first reaction rate change and the second reaction rate change are indicative of the presence or absence of the complex.

In yet another embodiment, the method comprises determining a first reaction rate change at a first wavelength and a second reaction rate change at a second wavelength, wherein the first wavelength is within the absorbance wavelength region and the second wavelength is within a scattering wavelength region and wherein the first reaction rate change and the second reaction rate change are indicative of the presence or absence of the complex.

In some embodiments, the reaction rate changes at the first wavelength and second wavelength can be measured at different time points. The first time point may be within an initial period of mixing the first reagent with the second reagent. A second time point may be within a last period of mixing the first reagent with the second reagent.

In other embodiments, a group of reaction rate changes at the first wavelength is determined for a plurality of time points and a group of reaction rate changes at the second wavelength is determined for a plurality of time points, wherein the integration of the first group of reaction rate changes or an integration of the second group of reaction rate changes is indicative of the presence or absence of the complex of the first reagent and the second reagent.

In some embodiments, the reaction rate changes may be determined in relation to an absorbance value corresponding to a reference wavelength. In one embodiment, the reference wavelength is a wavelength with minimum interference with absorbance or scattering of the first reagent, second reagent, and/or their complex. In another embodiment, the reference wavelength is a wavelength corresponding to an isosbestic point.

In another embodiment of the invention, the method comprises determining a first absorbance value at a first wavelength and a second absorbance value at a second wavelength upon mixing the first reagent with the second reagent, wherein the first wavelength is within the absorbance wavelength region and the second wavelength is within a scattering wavelength region; and comparing the first absorbance value to the second absorbance value, wherein the comparison of the values is indicative of the presence of the complex of the first reagent and the second reagent. In some embodiments, comparing the first absorbance value to the second absorbance value comprises determining the ratio of the first absorbance value to the second absorbance value.

In another embodiment, the method further comprises obtaining at least one measurement of reagent integrity, wherein the at least one measurement is indicative of non-specific signals. The measurements of reagent integrity may include determining for an initial time point of mixing the first reagent with the second reagent a transmittance value at a reference wavelength, a maximum absorbance value at a wavelength corresponding to $\lambda_{max}$, or combinations thereof. Such measurements may be compared to pre-determined limit values.

The present invention further provides algorithms for analyzing reaction rate data obtained from absorbance spectra to determine the presence or absence of a complex between a first reagent and a second reagent. In one embodiment, the algorithm computes the sum of the first and second reaction rate changes. In another embodiment, the algorithm computes the ratio of the sum of the first and second reaction rate change versus the sum of the third and fourth reaction rate change.

In some embodiments, the algorithm compares the sum of the reaction rate changes or the ratio of the sums of reaction rate changes to a predetermined threshold value. In some embodiments, the algorithm integrates a first group of reaction rate changes at a first wavelength and compares the integration to a predetermined threshold value.

In other embodiments, the algorithm integrates a second group of reaction rate changes at a second wavelength and compares the integration to a predetermined threshold value. In one embodiment, the first group of reaction rate changes are determined by subtracting an absorbance value of a control sample at the first wavelength from a first set of absorbance values corresponding to the first wavelength, and the second group of reaction rate changes are determined by subtracting an absorbance value of the control sample at the second wavelength from a second set of absorbance values corresponding to the second wavelength. In another embodiment, the first group of reaction rate changes are normalized based on an absorbance value of a control sample corresponding to the first wavelength and the second group of reaction rate changes are normalized based on an absorbance value of the control sample corresponding to the second wavelength.

In another embodiment, the first group of reaction rate changes are normalized based on an absorbance value of a control sample corresponding to the first wavelength at a first time point in the reaction period and the second group of reaction rate changes are normalized based on an absorbance value of the control sample corresponding to the second wavelength at the first time point in the reaction period.

In another embodiment, the first group of reaction rate changes are normalized based on an absorbance value corresponding to the first wavelength at a first time point in the reaction period and wherein the second group of reaction rate changes are normalized based on an absorbance value corresponding to the second wavelength at the first point in the reaction period.

In some embodiments, the algorithm calculates an average ratio of a first group of absorbance values to a second group of absorbance values, wherein the first group of absorbance values is determined at a first wavelength for a plurality of time points in an initial reaction period for mixing the first reagent with the second reagent, and the second group of absorbance values is determined at a second wavelength for said plurality of time points, wherein the first wavelength is within the absorbance wavelength region and the second wavelength is within a scattering wavelength region. The average ratio may be compared to a pre-determined threshold value. In another embodiment, the average ratio is compared to pre-determined high and low limit values.

In another embodiment, the first group of absorbance values are adjusted based on a first group of control absorbance values at the first wavelength for each of said plurality of time points and the second group of absorbance values are adjusted based on a second group of control absorbance values at the second wavelength for each of said plurality of time points. Control absorbance values are determined from control samples or control solutions, such as optical and sample blanks.

In yet another embodiment, the inventive method comprises determining the presence or absence of a complex of a first reagent and a second reagent in a mixture, wherein the first reagent is an analyte in a biological sample. In some embodiments, the second reagent is an entity that specifically binds to the first reagent. In other embodiments, the second reagent is an antibody that specifically binds to the analyte.

In one embodiment of the invention, the first or second reagent is conjugated to a detectable entity. The detectable entity may be metal nanoparticles or metal nanoshells including gold particles, silver particles, copper particles, platinum particles, composite particles, gold hollow spheres, gold-coated silica nanoshells, and silica-coated gold shells.

BRIEF DESCRIPTION OF THE DRAWINGS

FIG. 13. Absorbance spectra of gold nanoparticles coated with anti-heartworm antibodies in the presence of purified heartworm antigen at different time points in the reaction (0, 5, and 10 min). Note the decrease in peak absorbance at $\lambda_{max}$ and the broadening of the absorbance peak as the reaction progresses.

FIG. 18. Reaction rate plotted versus heartworm antigen concentration (expressed as dilution ratio) at 515 nm (diamonds) or 600 nm (triangles).

DETAILED DESCRIPTION OF THE INVENTION

Figure 1:
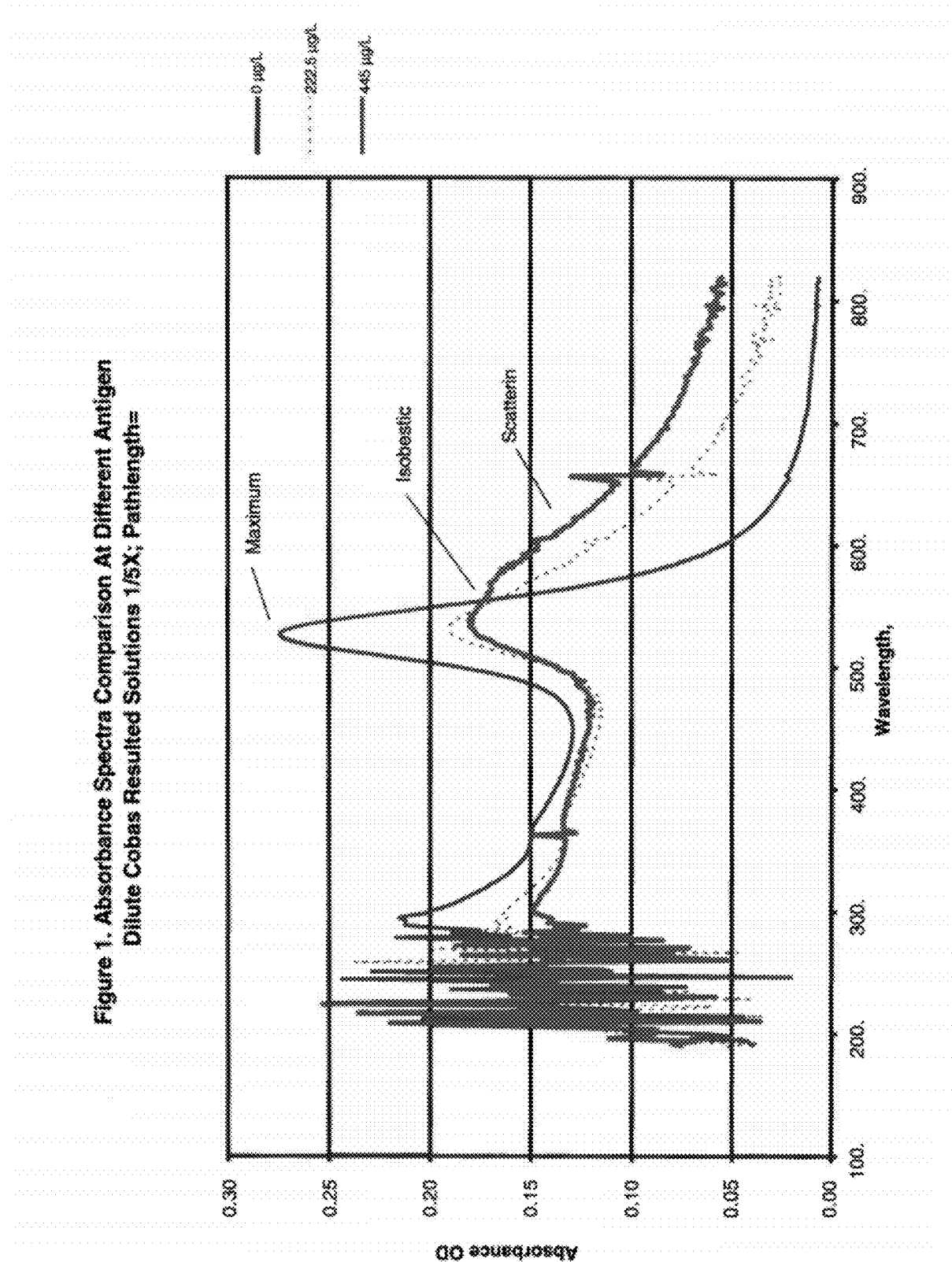
FIG. 1. Absorbance spectra of gold nanoparticles coated with anti-heartworm antibodies in the presence of 0, 223, or 445 µg/L of purified heartworm antigen.

The present invention provides methods for detecting the presence or absence of a complex between a first reagent and a second reagent. These methods can be employed to identify binding partners of known molecules as well as to detect specific analytes in solution. In particular, the inventive methods pose a solution to the problem of accurate and sensitive detection of analytes in complex biological solutions.

The methods of the present invention utilize the phenomenon of local surface plasmon resonance observed in monodispersed metal nanoparticles. Detection of a particular analyte is achieved by measuring reaction rate changes from absorbance spectra of metal nanoparticles conjugated to a binding partner of the analyte of interest. Non-specific binding can be eliminated by measuring reaction rates at multiple wavelengths.

Several types of complexes may be detected and quantified using the methods of the present invention by conjugating either the first reagent or second reagent to a detectable entity, such as a metal nanoparticle. The first reagent may be an analyte in solution, while the second reagent is a binding partner or entity that specifically recognizes that analyte. For example, the analyte may be an antigen and the binding partner may be an antibody to that particular antigen. Other examples of complexes that may be detected include, but are not limited to, DNA/DNA, DNA/RNA, RNA/RNA, nucleic acid/protein, and receptor/ligand complexes. In one embodiment of the invention, an antigen/antibody complex is detected, wherein the second reagent is an antibody conjugated to a detectable entity.

A "detectable entity" is an entity that exhibits wavelength selective absorption in the ultra-violet, visible, or near infrared electromagnetic spectrum and scatters incident radiation. Detectable entities suitable for use in the methods of the present invention include metallic nanoparticles and metal nanoshells. Various types of metal nanoparticles that may be conjugated to either the first reagent or second reagent include, but are not limited to, gold particles, silver particles, copper particles, platinum particles, composite particles, and gold hollow spheres. Additionally, metal nanoshells as described in U.S. Pat. No. 6,699,724, which is herein incorporated by reference in its entirety, can also be used as the labeling particles. Metal nanoshells are particles comprised of a dielectric core and a metallic coating that have a defined core radius to shell thickness ratio. The core can be comprised of a variety of materials including silicon dioxide, gold sulfide, titanium dioxide, and polystyrene. Suitable metals for the shell include gold, silver, copper, platinum, palladium, lead, and iron. Gold-coated silica nanoshells or silica-coated gold shells are preferred in some embodiments.

The optical properties of the particles depend largely on particle diameter. For solid gold particles, the maximum absorption wavelength ($\lambda_{max}$) is from about 515 nm to about 560 nm depending on particle size. Gold particles having a 30 nm diameter maximally absorb at about 520 nm with $\lambda_{max}$ shifting to longer wavelengths as particle diameter increases. Silver and copper particles have a $\lambda_{max}$ in the ultra-violet/blue or red region (e.g. from about 350 nm to about 500 nm) with increasing particle diameter causing a shift in $\lambda_{max}$ to longer wavelengths. Metallic nanoparticles with diameters from about 10 nm to about 100 nm are preferable.

In the case of nanoshells, core radius to shell thickness ratio also dictates the particle's optical resonance. For example, for gold-coated silica nanoshells, decreases in the core radius to shell thickness ratio produces shifts of $\lambda_{max}$ to shorter wavelengths. Nanoshells suitable for use in the methods of the invention typically have core diameters ranging from about 1 nm to about 4 µm and shell thicknesses ranging from about 1 nm to about 100 nm.

Methods of conjugating metal nanoparticles or metal nanoshells to macromolecules are well known in the art. One possible method is by passive adsorption. This method involves adjusting the pH of the metal colloid solution to a pH at which the protein to be labeled has a positive charge, mixing the metal colloid solution with the protein solution, and centrifuging the resultant mixture. The labeled protein is then obtained by removing the supernatant and resolubilizing the precipitate. Other methods of conjugating macromolecules to metal nanoparticles or nanoshells are known to the skilled artisan, who can select the proper method based on the type of desired nanoparticle to be used and the type of macromolecule to be labeled.

The methods disclosed herein are suitable for use with any agents that accelerate a spectral shift upon binding of an analyte to a binding partner coupled to a detectable entity. Such agents include, but are not limited to, various types of polymers, such as PEG, PVA (polyvinyl alcohol), and PVP (polyvinylpyrrolidone).

The present invention provides a method for determining the presence or absence of a complex of a first reagent and a second reagent in a mixture. In one embodiment, the method comprises determining a reaction rate change corresponding to a wavelength within an absorbance wavelength region upon mixing the first reagent with the second reagent, wherein the reaction rate change is indicative of the presence or absence of the complex of the first reagent and the second reagent.

The reaction rate change may be positive or negative, e.g., depending on whether a detection is directed to an increase or decrease of a complex of a first reagent and a second reagent. In some embodiments, one can detect the increase of a complex formed between a first reagent and a second reagent, e.g., direct detection of the complex without further processing such as separating it from reagents. Such detection usually produces a positive rate change associated with an increase of the complex. In some embodiments, one can detect the decrease of a complex formed between a first reagent and a second reagent. For example, one can detect the decrease or "disappearing" of the complex after separating some or all of the complexes from the reagents, e.g., via centrifugal force, etc. Such detection usually produces a negative rate change associated with a decrease of the complex. Either positive or negative reaction rate changes can be used to indicate the presence or absence of a complex between a first reagent and a second reagent under various reaction conditions.

In another embodiment, the method further comprises determining a second reaction rate change at a second wavelength, wherein the second wavelength is in the absorbance wavelength region and wherein the first and second reaction rate change are indicative of the presence or absence of the complex of the first reagent and second reagent.

In still another embodiment, the first wavelength is in the absorbance wavelength region and the second wavelength is in the scattering wavelength region and the first and second reaction rate changes are indicative of the presence or absence of the complex.

The absorbance and scattering wavelength regions will be determined by the type of detectable entity conjugated to the first or second reagent. As described above, different metallic nanoparticles or nanoshells exhibit different optical properties based on their size and composition. The absorbance wavelength region may be from about 280 nm to about 550 nm. The scattering wavelength region may be from about 550 nm to about 800 nm. The precise absorbance and scattering wavelength regions for each selected metal particle conjugate are easily determinable by the skilled artisan.

The reaction rate changes may be calculated by measuring the absorbance value at a selected wavelength within the absorbance and/or scattering wavelength region and the absorbance value at a reference wavelength. The reference wavelength is a wavelength with minimum interference with absorbance or scattering of the first reagent, second reagent, and/or their complex. Thus, the absorbance value at the reference wavelength is not affected by the presence of the first reagent, second reagent, or the complex of the first reagent and second reagent and can be used to eliminate absorbance or scattering due to fluctuations in the light source or non-specific interactions.

In one embodiment, the reference wavelength is a wavelength outside the visible portion of the electromagnetic spectrum (i.e. greater than 700 nm). In another embodiment, the reference wavelength is 850 nm. In yet another embodiment, the reference wavelength is a wavelength corresponding to an isosbestic point.

An "isosbestic point" is a specific wavelength at which two or more species have the same absorptivity. The absorbance of a reaction mixture at the wavelength corresponding to the isosbestic point does not change over the course of the reaction as long as the reaction does not cause precipitation or molecular structure disruption.

According to another embodiment of the present invention, the method comprises determining for a first time point a first reaction rate change at a first wavelength and a second reaction rate change at a second wavelength, determining for a second time point a third reaction rate change at the first wavelength and a fourth reaction rate change at the second wavelength, wherein the first and second wavelength are within the absorbance wavelength region and wherein the first, second, third, and fourth reaction rate change are indicative of the presence or absence of the complex. In one embodiment, said first and third reaction rate changes are determined at a first wavelength and said second and fourth reaction rate changes are determined at a second wavelength, wherein the first wavelength is within the absorbance wavelength region and the second wavelength is within the scattering region.

In another embodiment, the first time point is within an initial period of mixing the first reagent with the second reagent and that the second time point is within a last period of mixing the first reagent with the second reagent. The first time point may be about 30 seconds, about 1 minute, about 2 minutes, about 3 minutes, about 4 minutes, or about 5 minutes upon mixing the first reagent with the second reagent. The second time point may be about 4 minutes, about 6 minutes, about 8 minutes, about 10 minutes, or about 12 minutes upon mixing the first reagent with the second reagent.

In some embodiments of the invention, the method comprises determining a first absorbance value at a first wavelength and a second absorbance value at a second wavelength upon mixing the first reagent with the second reagent, wherein the first wavelength is within the absorbance wavelength region and the second wavelength is within a scattering wavelength region; and comparing the first absorbance value to the second absorbance value, wherein the comparison of the values is indicative of the presence of the complex of the first reagent and the second reagent.

A comparison of the first absorbance value to the second absorbance value may comprise determining a ratio of the first absorbance value to the second absorbance value, a difference between the first and second absorbance values, or any other suitable mathematical calculation and/or comparison. In one embodiment, comparing the first absorbance value to the second absorbance value comprises determining the ratio of the first absorbance value to the second absorbance value.

The first and second absorbance values may be determined relative to a reference wavelength as described herein. In one embodiment, the first and second absorbance values are normalized to the maximum absorbance value at a wavelength corresponding to $\lambda_{max}$. The maximum absorbance or peak absorbance for a substance occurs at the $\lambda_{max}$ wavelength. The change in peak absorbance or the absorbance at $\lambda_{max}$ may be indicative of the presence of a complex between the first reagent and the second reagent. Thus, in another embodiment of the invention, the method comprises measuring for a first time point a first absorbance value at $\lambda_{max}$, measuring for a second time point a second absorbance value at $\lambda_{max}$, and comparing the first and second absorbance values, wherein a difference in the first and second absorbance values is indicative of a complex between the first reagent and the second reagent. Preferably the first time point is within an initial period of mixing the first reagent and the second reagent and the second time point is within a last period of mixing the first reagent and the second reagent.

In other embodiments of the invention, the method further comprises obtaining at least one measurement of reagent integrity, wherein the at least one measurement is indicative of non-specific signals. "Reagent integrity" refers to characteristics or properties of reagents or mixtures of reagents, such as absorbance, temperature, color, etc. that are expected to be in a standard range of values for a particular reagent. "Non-specific signals" refer to absorbance values or changes in absorbance values that are not due to the binding of the first reagent to the second reagent. Non-specific signals can include, but are not limited to signals resulting from components in the sample interacting with the first reagent and/or the second reagent, instrument errors in detecting and measuring absorbance, or complications due to the detectable entity or means of detecting the detectable entity (e.g. light source).

In one embodiment, the at least one measurement comprises determining a transmittance value at a reference wavelength at an initial time point of mixing the first reagent with the second reagent; and comparing the transmittance value to a pre-determined limit value. The pre-determined limit value may be based on transmittance values at a reference wavelength from multiple reactions.

In another embodiment, the at least one measurement comprises determining a maximum absorbance value at a wavelength corresponding to $\lambda_{max}$ at an initial time point of mixing the first reagent with the second reagent; and comparing the maximum absorbance to a pre-determined high absorbance limit value or a pre-determined low absorbance limit value. In some embodiments, the pre-determined high absorbance and low absorbance limit values may be based on maximum and minimum limits of detection for a particular instrument.

In yet another embodiment of the invention, the method comprises determining a first group of absorbance values at a first wavelength for a plurality of time points in an initial reaction period for mixing the first reagent with the second reagent, determining a second group of absorbance values at a second wavelength for said plurality of time points, wherein the first wavelength is within the absorbance wavelength region and the second wavelength is within a scattering wavelength region; and comparing the average of the first group of absorbance values to the average of the second group of absorbance values, wherein the comparison of the average absorbance values is indicative of the presence of the complex of the first reagent and the second reagent. Comparing the average of the first group of absorbance values to the average of the second group of absorbance values may comprise any suitable mathematical comparison and/or calculation, such as a ratio, difference score, ranking, etc. In one embodiment, comparing the average absorbance values comprises determining the average ratio of the first group of absorbance values to the second group of absorbance values.

The present invention also encompasses algorithms for analyzing absorbance values or the reaction rate data obtained from absorbance spectra as described above to determine whether a complex between a first reagent and second reagent is formed. The first algorithm, termed logic #1, is used in conditions of high reactivity between the first and second reagents. The second algorithm, logic #2, is particularly useful when there is low reactivity between the first and second reagents and an isosbestic point can be identified in the absorbance spectra. The third algorithm, logic #3, is particularly suitable for low reactivity conditions when no isosbestic point can be determined from the absorbance spectra. Each of the algorithms can be used independently or in combination. For example, if a negative outcome is concluded after performing the first algorithm, the second algorithm can be employed to eliminate the possibility of a false negative. Similarly, the third algorithm can be employed to confirm a positive result obtained from the second algorithm.

Several analysis options are available under the first algorithm (logic #1). In one embodiment, the sum of the first and second reaction rate changes are compared to a first predetermined threshold value. In another embodiment, the ratio of the sum of the first and second reaction rate change versus the sum of the third and fourth reaction rate change is compared to a second predetermined threshold value. In another embodiment, the sum of the first and second reaction rate change are compared to a first predetermined threshold value, and the ratio of the sum of the first and second reaction rate change versus the sum of the third and fourth reaction rate change is compared to a second predetermined threshold value, wherein the comparison to the first predetermined threshold value and the second predetermined threshold value are indicative of the presence or absence of the complex.

The threshold values may be determined from the maximum signals generated from negative samples or control solutions. The threshold values may be further adjusted to account for assay imprecision. If the calculated sum and/or ratio exceeds its corresponding predetermined threshold value, then the sample is "positive". A "positive" sample means that a complex was detected between the first and second reagents. If the calculated sum and/or ratio is equal to or less than the predetermined threshold value, then the sample is "negative". A "negative" sample means that a complex between the first reagent and the second reagent was not detected. An example of the use of the first algorithm to detect an analyte in a biological sample is shown in Example 2.

As mentioned previously, the second algorithm (logic #2) is useful for detecting the presence of a complex between a first reagent and a second reagent when the reactivity between the two reagents is relatively low. In one embodiment, the method comprises determining a first group of reaction rate changes at a first wavelength for a plurality of time points of a reaction period for mixing the first reagent with the second reagent, determining a second group of reaction rate changes at a second wavelength for said plurality of time points, wherein the first wavelength is within the absorbance wavelength region and wherein the second wavelength is within a scattering wavelength region, and wherein an integration of the first group of reaction rate changes or an integration of the second group of reaction rate changes is indicative of the presence or absence of the complex of the first reagent and the second reagent. The integration of the first group of reaction rate changes and/or the integration of the second group of reaction rate changes may be compared to a predetermined threshold value.

Similar to the first algorithm, the threshold values may be determined from negative samples or control samples and further adjusted to account for imprecision of the measurements. If the integration of the first group of reaction rate changes or the integration of the second group of reaction rate changes exceeds the predetermined threshold value, then the sample is reported as positive. If the integration values are equal to or less than the predetermined threshold value, then the sample is reported as negative.

In one embodiment, the first group of reaction rate changes are determined based on a first set of absorbance values corresponding to the first wavelength and a reference absorbance value corresponding to a reference wavelength while the second group of reaction rate changes are determined based on a second set of absorbance values corresponding to the second wavelength and the reference absorbance value. In some embodiments, the reference wavelength is a wavelength corresponding to an isosbestic point.

In another embodiment, the first group of reaction rate changes are determined by subtracting an absorbance value of a control sample at the first wavelength from a first set of absorbance values corresponding to the first wavelength, and the second group of reaction rate changes are determined by subtracting an absorbance value of the control sample at the second wavelength from a second set of absorbance values corresponding to the second wavelength.

In another embodiment, the first group of reaction rate changes are normalized based on an absorbance value of a control sample corresponding to the first wavelength and the second group of reaction rate changes are normalized based on an absorbance value of the control sample corresponding to the second wavelength.

In yet another embodiment, the first group of reaction rate changes are normalized based on an absorbance value of a control sample corresponding to the first wavelength at a first time point in the reaction period and the second group of reaction rate changes are normalized based on an absorbance value of the control sample corresponding to the second wavelength at the first time point in the reaction period.

In still another embodiment, the first group of reaction rate changes are normalized based on an absorbance value corresponding to the first wavelength at a first time point in the reaction period and the second group of reaction rate changes are normalized based on an absorbance value corresponding to the second wavelength at the first point in the reaction period.

The third algorithm (logic #3) employs a ratio of an absorbance value at a first wavelength in the absorbance region to an absorbance value at a second wavelength in the scattering region to determine the presence of a complex between the first reagent and the second reagent. This algorithm is particularly useful when an isosbestic point cannot be identified from the absorbance spectra and when the reactivity between the first reagent and the second reagent is low. In one embodiment, the method comprises determining a first group of absorbance values at a first wavelength for a plurality of time points in an initial reaction period for mixing the first reagent with the second reagent, determining a second group of absorbance values at a second wavelength for said plurality of time points, wherein the first wavelength is within the absorbance wavelength region and the second wavelength is within a scattering wavelength region; and determining the average ratio of the first group of absorbance values to the second group of absorbance values, wherein a change in the average ratio of the absorbance values is indicative of the presence of the complex of the first reagent and the second reagent. The average ratio may be compared to a pre-determined threshold value or cut-off value.

As described for the first and second algorithms, the threshold value may be determined from negative samples or control samples and further adjusted to account for imprecision of the measurements. In some embodiments, if the average ratio of the first group of absorbance values to the second group of absorbance values, wherein the first group of absorbance values is at a wavelength in the absorbance region and the second group of absorbance values is at a wavelength in the scattering region, is less than the threshold level, then the sample is reported as positive. In other embodiments, if the average ratio of the second group of absorbance values to the first group of absorbance values, wherein the second group of absorbance values is at a wavelength in the scattering region and the first group of absorbance values is at a wavelength in the absorbance region, is greater than the threshold level, then the sample is reported as positive.

In one embodiment, the average ratio is compared to a pre-determined high ratio limit value or a pre-determined low ratio limit value. The pre-determined high ratio and low ratio limit values may be determined by absorbance values from negative control samples, such as those containing only the second reagent (e.g. detectable entity) or samples containing a high concentration of the first and second reagents. By way of example, a negative control sample may contain only gold nanoparticles conjugated to a detection antibody, while a positive control sample may contain a high concentration of antigen that is bound by the detection antibody.

In another embodiment, the first group of absorbance values are adjusted based on a first group of control absorbance values at the first wavelength for each of said plurality of time points and the second group of absorbance values are adjusted based on a second group of control absorbance values at the second wavelength for each of said plurality of time points. "Control absorbance values" may be obtained from a control solution or control sample.

A "control solution" or "control sample" can be a solution or sample which provides a "background" reading or a reading associated with non-analyte caused signal. For example, a control solution or sample can be a mixture containing all components of a reaction except for the first reagent, second reagent, or both. Alternatively a control sample can be a "blanked sample", which includes just a sample, but not any reaction reagents or buffer. In addition, a control sample can be a buffer containing a sample to be tested without the presence of a first reagent, second reagent or both. The control solution or control sample can also be a solution containing only the first reagent or second reagent with none of the remaining components of the reaction. In some instances, the control solution or control sample may be an empty reaction container (e.g. empty cuvette). In other embodiments, the control solution or control sample may be an optical blank, in which only the detectable entity is present.

Any of the methods described herein may be used to determine the quantity of a complex between a first reagent and a second reagent. Such methods are particularly useful for determining the approximate amount of analyte in a sample, which can be used inter alia to diagnose certain medical conditions or evaluate the efficacy of a drug therapy. In one embodiment, determining the quantity of a complex between a first reagent and a second reagent comprises establishing a standard curve for the particular complex by measuring reaction rates and/or absorbance ratios according to the methods described herein for samples with a known quantity of complex; determining the reaction rate and/or absorbance ratio for a test sample; and comparing the reaction rate and/or absorbance ratio for the test sample to the values obtained for the standard curve, thereby determining the quantity of the complex between the first reagent and the second reagent. In some embodiments, determining the quantity of a complex between a first reagent and a second reagent comprises comparing the absorbance ratio and/or reaction rate from a test sample to the absorbance ratio and/or reaction rate from one sample with a known quantity of complex, thereby determining the quantity of the complex in the test sample. The quantitative values obtained from test samples may be compared to pre-determined threshold values, wherein said pre-determined threshold values are indicative of either an abnormal or normal level of the complex (e.g. analyte in sample).

Various means for measuring the absorbance values at different wavelengths are known in the art. Any spectrophotometric or photometric instruments are suitable for use in the disclosed methods. Some non-limiting examples include plate readers, Cobas Fara analyzers, and Piccolo® xpress analyzers, Vetscan, optic fiber readers, centrifugal analyzers from Olympus, Hitachi etc. All calculations required for use in the inventive methods can be performed by independent software or software integrated into the instrument used for acquiring the absorbance data.

In some embodiments, the first reagent is an analyte in a biological sample. Thus, the present invention encompasses methods of detecting the presence of an analyte in a biological sample, such as blood, plasma, serum, urine, bile, cerebrospinal fluid, and saliva. In another embodiment, the second reagent is an entity that specifically binds to the first reagent. In another embodiment, the second reagent is an antibody that specifically binds to the analyte. In still another embodiment, the second reagent is an antibody conjugated to a detectable entity.

Several different types of analytes may be detected with the methods of the invention, particularly those that are significant in the diagnoses of diseases. Some examples of types of analytes include, but are not limited to, proteins (e.g. hormones, enzymes), glycoproteins, peptides, small molecules, polysaccharides, antibodies, nucleic acids, drugs, toxins, viruses, virus particles, and portions of a cell wall. In some embodiments of the invention, the presence or absence of the analytes predicts the presence or absence of a disease or infection in animals or humans. Several diseases, such as canine monocytic ehrlichiosis, lyme disease, anaplasmosis, influenza, and Legionnaires' disease could be diagnosed using the detection methods presented herein. Some non-limiting examples of such analytes include eptitopes of heartworm, *Ehrlichia canis, Borrelia burgdorferi, Borrelia afzelii, Borrelia garinii, Anaplasma phagocytophilum*, feline leukemia virus, parvovirus, influenza viral A and B strains, avian influenza virus, respiratory syncytial virus, *Legionella*, adenovirus, Group A *Streptococcus*, and other bacteria or viruses known to cause disease in animals or humans. Any antigen/antibody complex could be detected in a biological sample with the methods of the invention.

The present invention also contemplates the detection of multiple analytes simultaneously. Distinct absorbance and scattering wavelength regions can be obtained for detection of each analyte by using different size nanoparticles or nanoparticles comprised of different metals for conjugation to each type of binding partner. The following non-limiting example illustrates one possible embodiment. A first antibody, which recognizes a first analyte is conjugated to a silver nanoparticle, and a second antibody, which recognizes a second analyte, is conjugated to a gold nanoparticle. The maximum absorbance wavelength for the first antibody would be in the ultra-violet/blue region of the electromagnetic spectrum (e.g. 350 nm to 450 nm), while the maximum absorbance wavelength for the second antibody would be in the range of 515 nm to 560 nm. Multiple measurements at different wavelengths and various time points would allow one to detect the formation of a specific binding complex between the first antibody and the first analyte and/or the second antibody and the second analyte, while eliminating any signals due to non-specific interactions between the reagents and background components. Combinations of metal nanoparticles and metal nanoshells may also be used as the detectable entity to select absorbance and scattering wavelength regions for detection of a set of analytes.

Alternatively, multiple analytes may be detected simultaneously by measuring absorbance values at multiple wavelengths and time points for each of a plurality of reaction containers comprising binding partners for distinct analytes. By way of example, a first reaction container may comprise a first binding partner conjugated to a detectable entity for analyzing a first analyte, and a second reaction container may comprise a second binding partner conjugated to a detectable entity for analyzing a second analyte, wherein the first and second analytes are different. The detectable entities conjugated to the different binding partners in each of the reaction containers may be the same or they may be different. The number of analytes that can be detected simultaneously is only limited by the number of reaction containers that can be accommodated in the instrument monitoring absorbance.

EXAMPLES

Example 1

Homogenous Canine Heart Worm Assay

Anti-heartworm antibodies were procured from several sources such as Capricorn Products, Custom Monoclonals and ICL labs. IgG, IgM IgY antibodies to *Dirofilaria immitis*, commonly known as heartworm, were used to coat gold nanoparticles. Colloidal gold particles (37 nm in diameter) were coated with anti-heartworm antibodies by passive adsorption using standard techniques. A typical assay in a simple format was setup by mixing gold conjugates, buffer, sodium chloride and high molecular polyethylene glycols. Spectra of gold-conjugates following 10 min incubation with 0, 223 or 445 µg/L of a purified heartworm antigen (Capricorn Products) were obtained and are shown in FIG. 1.

For 0 µg/L, a very sharp and narrow peak at 530 nm suggested the conjugates are nearly mono-dispersed. With increasing antigen concentration, the absorbance peak at 530 nm declined with a concomitant increase in scattering peak (600 nm). An important feature of such spectra was that the spectral curves produced by various concentrations of the heartworm antigen intersected at 550 nm producing an isosbestic point.

Figure 2:
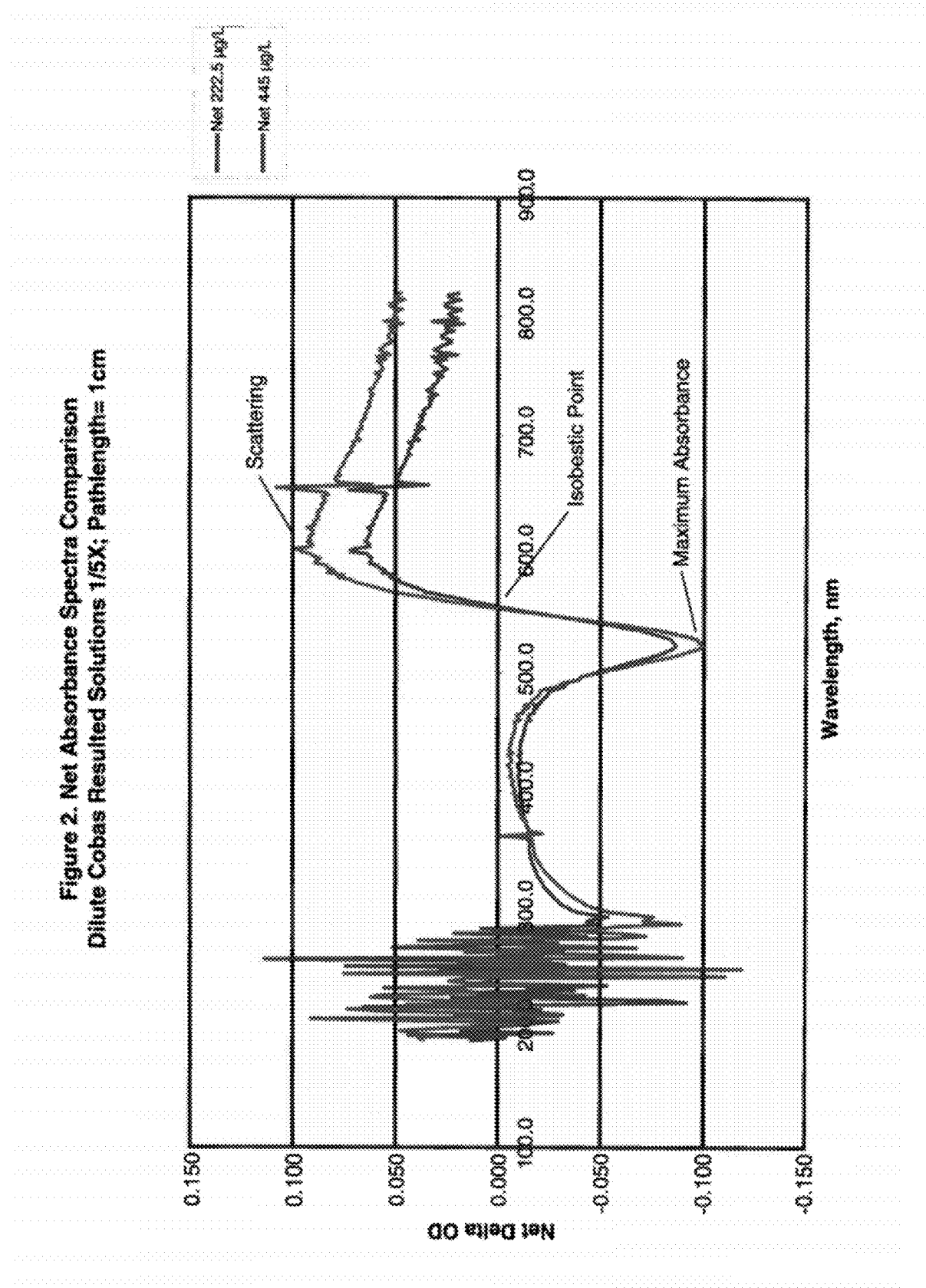
FIG. 2. Net Absorbance spectra showing the resulting absorbance difference between anti-heartworm antibody-coated nanoparticles in the presence and absence of different concentrations of heartworm antigen.

It was discovered that the plots of net spectral changes upon incubation of gold-antibody conjugates with the heartworm antigen were significantly more informative in distinguishing positive samples from those without the analyte. As shown in FIG. 2, the reaction rate changes in the absorbance and scattering regions are highly specific when they are referenced to the isosbestic point. The absorbance changes of the isosbestic point appears simply to be a function of sol-particle concentration.

Figure 3:
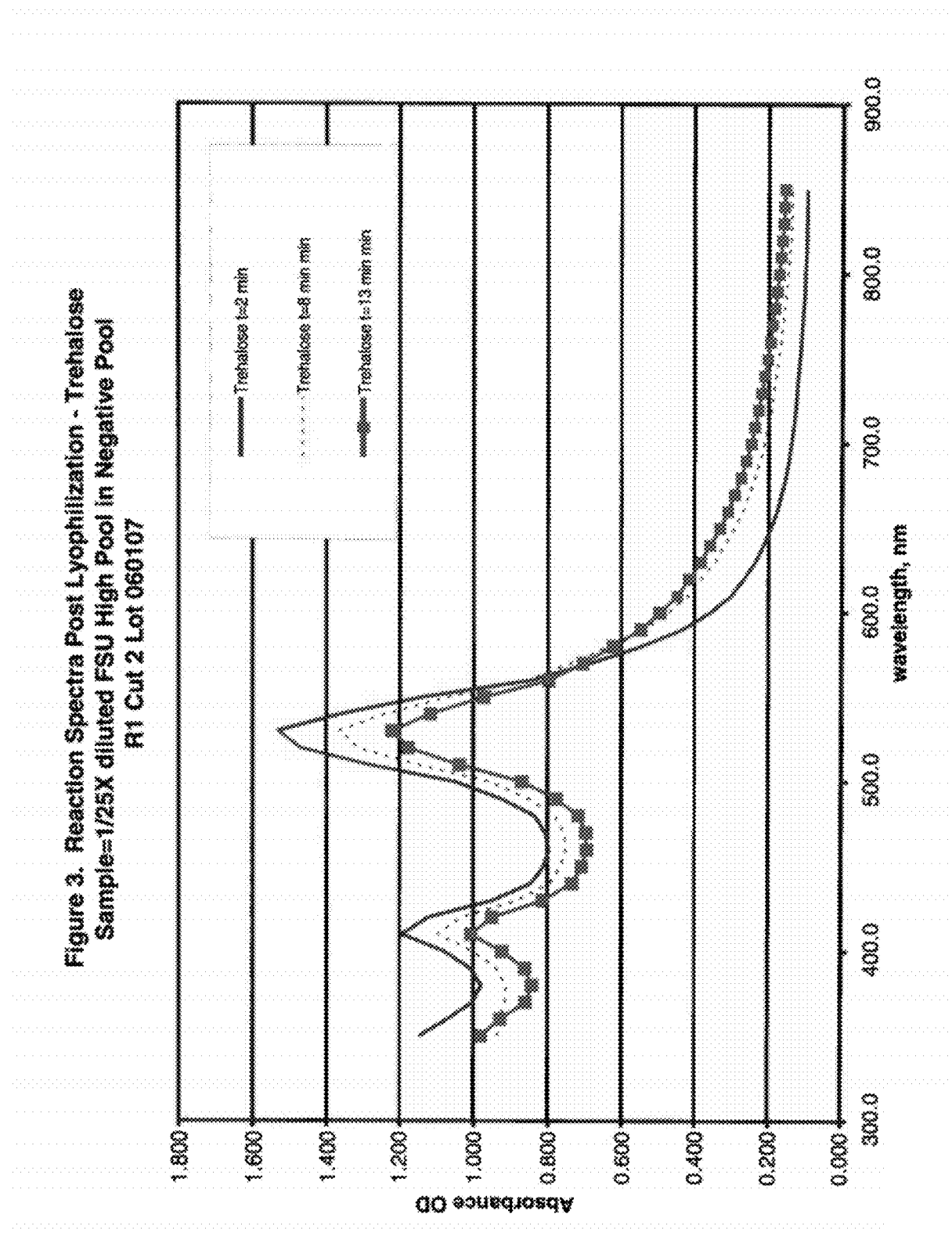
FIG. 3. Absorbance spectra from different time points (2, 8, and 13 min) following incubation of gold-antibody conjugates with heartworm antigen.
Figure 4:
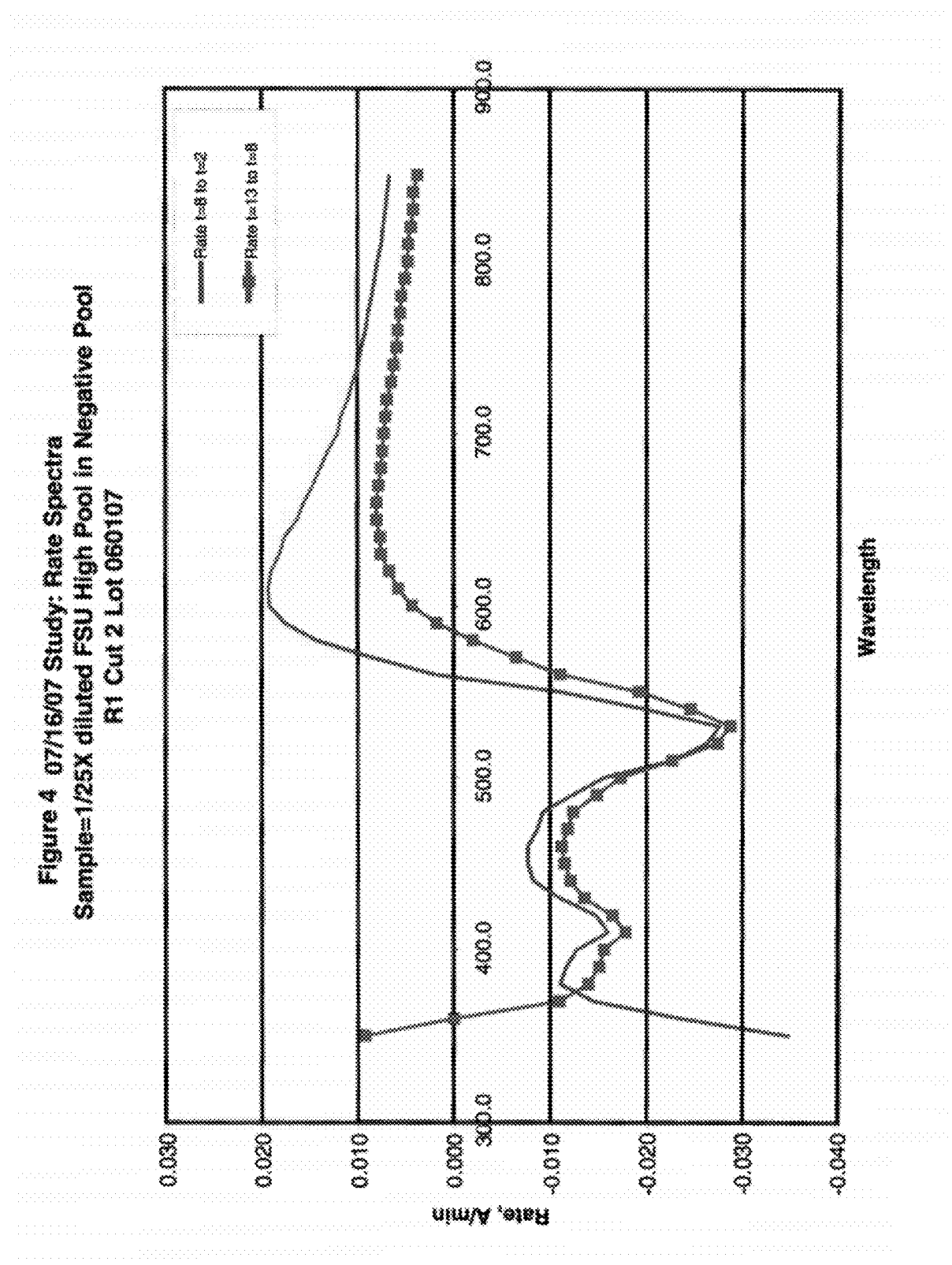
FIG. 4. Rate spectra for two different time intervals (2 to 8 min and 8 to 13 min) in the reaction of gold-antibody conjugates and heartworm antigen.

Another interesting feature that we observed was that the reaction rate was generally much faster in the beginning of the reaction and tapered down with time (FIG. 3). Numerical manipulations of such data brought forth the surprising discovery that the ratios of the initial and final rates further assisted in maximizing the differences between a negative sample and a sample containing analyte. The reaction spectra after 2, 8, and 13 minutes of incubating gold antibody conjugates with heartworm antigen are shown in FIG. 3. The secondary absorbance peak at 405 nm is most likely due to hemolysis from sample. FIG. 4 illustrates the rate comparison between two time intervals: t=2 to 8 min and t=8 to 13 min. Reaction rate in the scattering region (>550 nm) was clearly slower at the later phase of reaction.

Example 2

Algorithm for Identifying Positive Samples when Reactivity Between Analyte and Conjugate is High—Logic #1

Figure 20:
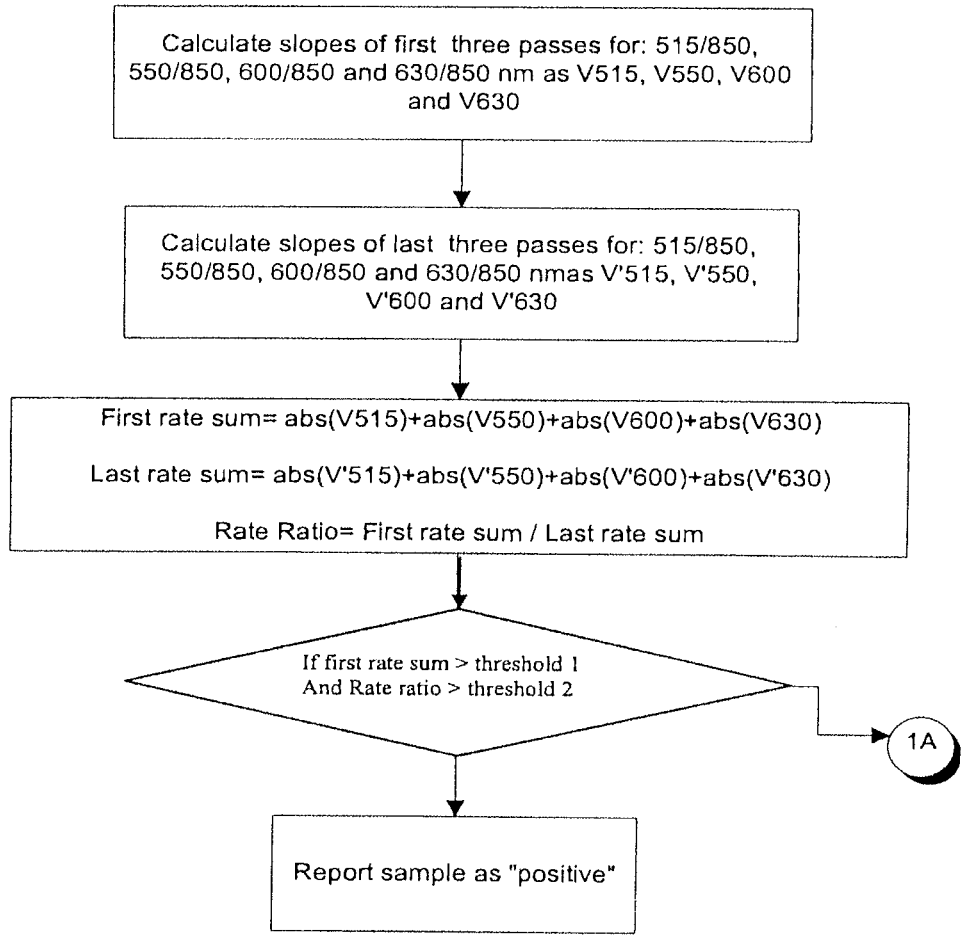
FIG. 20. Flow chart for the algorithm used in identifying positive samples when reactivity between analyte and conjugate is high (Logic #1).

For samples that show significant reactivity to the conjugate, the following logic can be applied. Initial and final rates are calculated in the absorbance (515 and 550 nm) and scattering (600 and 630 nm) regions. Since significant signals are generated from high positive samples, qualitative decisions are easily made by simply adding up all the initial rates. Additionally or alternatively, the rate ratio can be compared to distinguish negative from high positive samples. The threshold can be determined by maximum signals generated from negative samples and then further adjusted by the assay imprecision. The algorithm (Logic #1) is described in the flowchart shown in FIG. 20.

Figure 5:
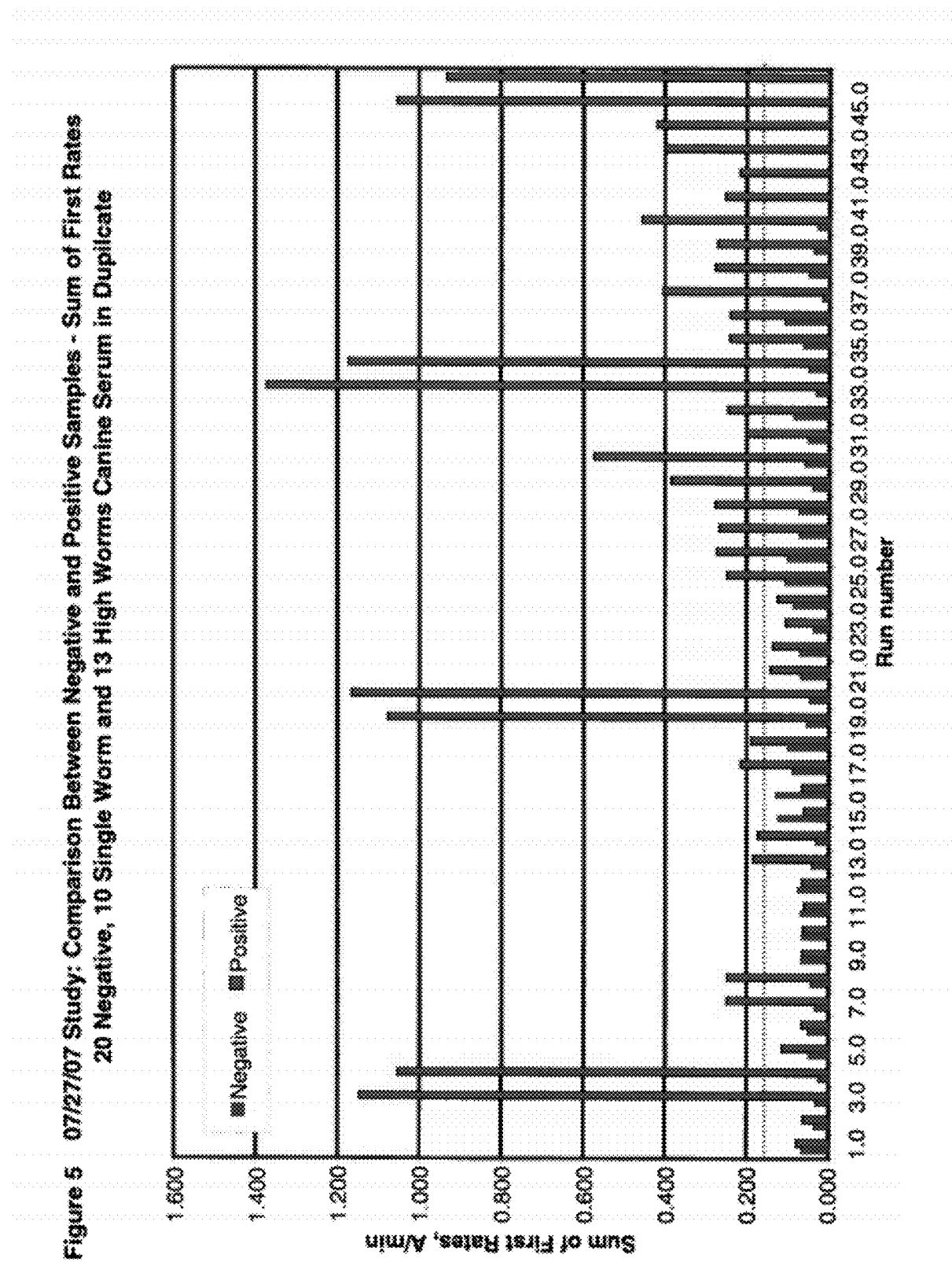
FIG. 5. Sum of initial rates calculated according to Logic #1 for negative and positive canine heartworm samples. The dotted line indicates the threshold level.
Figure 6:
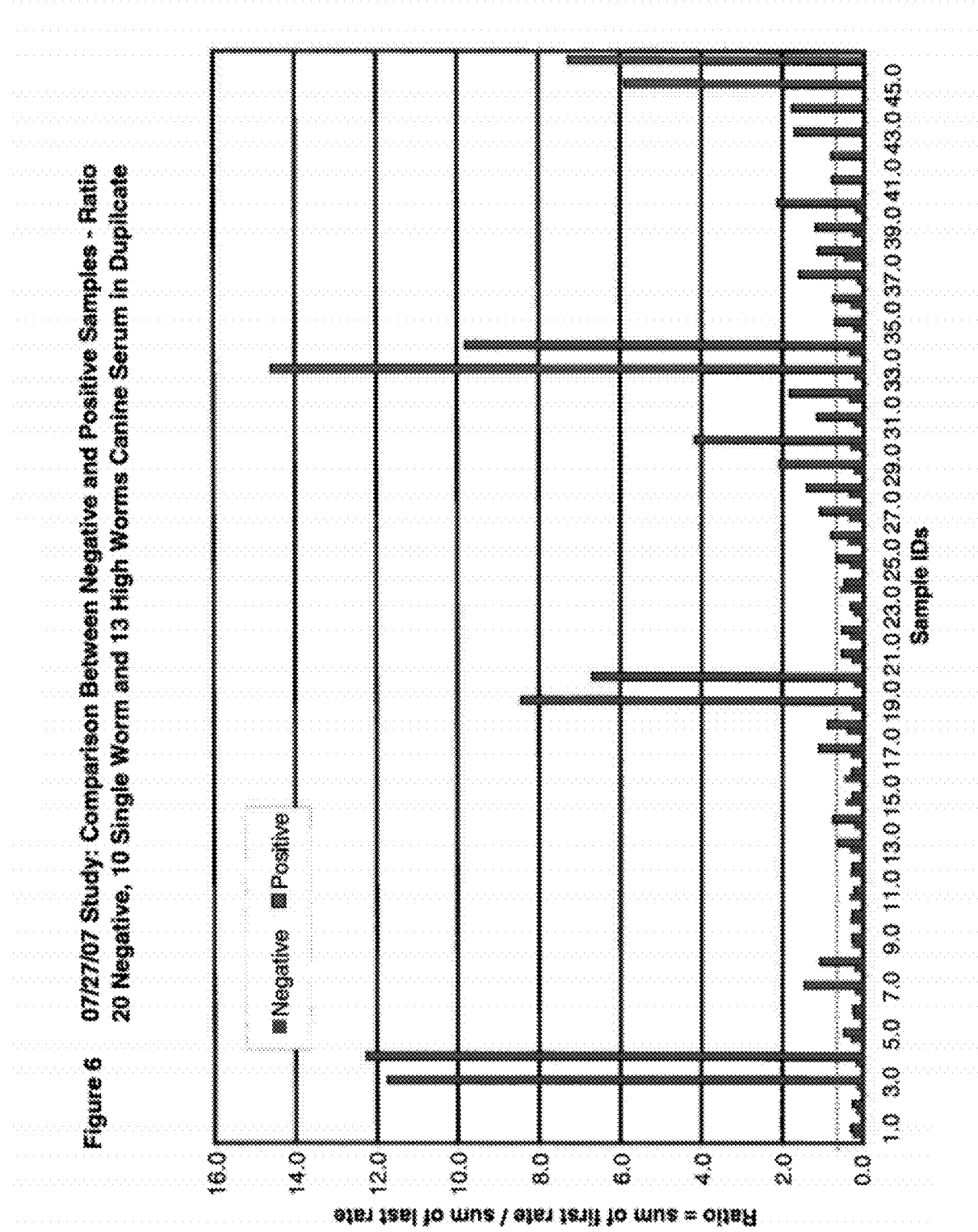
FIG. 6. Rate ratios calculated according to Logic #1 for negative and positive canine heartworm samples. The dotted line indicates the threshold level.

FIGS. 5 and 6 illustrate the first rate sum and rate ratio comparison, respectively, between positive and negative canine heartworm (CHW) samples. The threshold for these experiments was established from the maximal signals observed in negative samples plus three standard deviations of between-run error. Table 1 summarizes the number of samples identified as positive for CHW using Logic #1.

TABLE 1

Summary of samples identified positive for CHW using the Logic #1 algorithm.

| | Run number | ID Positive? | % |
|---|---|---|---|
| Negative | 40 | 0 | 0.0% |
| Single worm | 20 | 11 | 55.0% |
| High worms | 26 | 24 | 92.3% |

As shown by the results summarized in Table 1, the majority of positive samples could be identified when high reactivity between antigen and conjugate was observed.

Example 3

Algorithm for Identifying Positive Samples when Reactivity Between Analyte and Conjugate is Low—Logic #2

Figure 7:
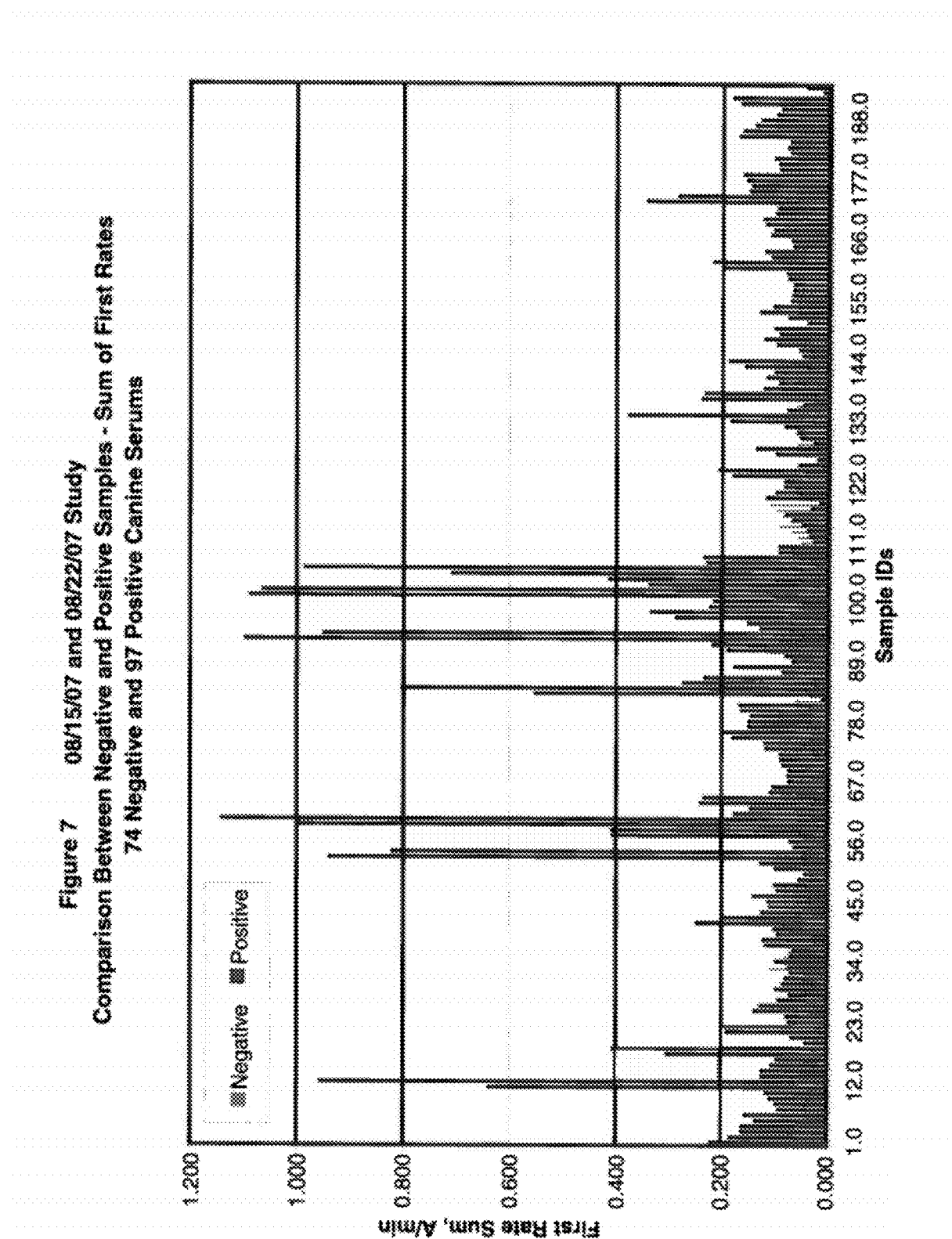
FIG. 7. Sum of initial rates calculated according to Logic #1 for negative and positive canine heartworm samples under conditions of low reactivity. The dotted line indicates the threshold level.

When sample and/or conjugate reactivity is very low, positive samples are difficult to identify using Logic #1. For example, FIG. 7 illustrates first-rate-sum results from positive samples that exhibited very low reactivity and rate due to sample aging. As can be seen from the results depicted in FIG. 7, the positive samples are not easily distinguished from negative samples using the first logic.

Figure 8:
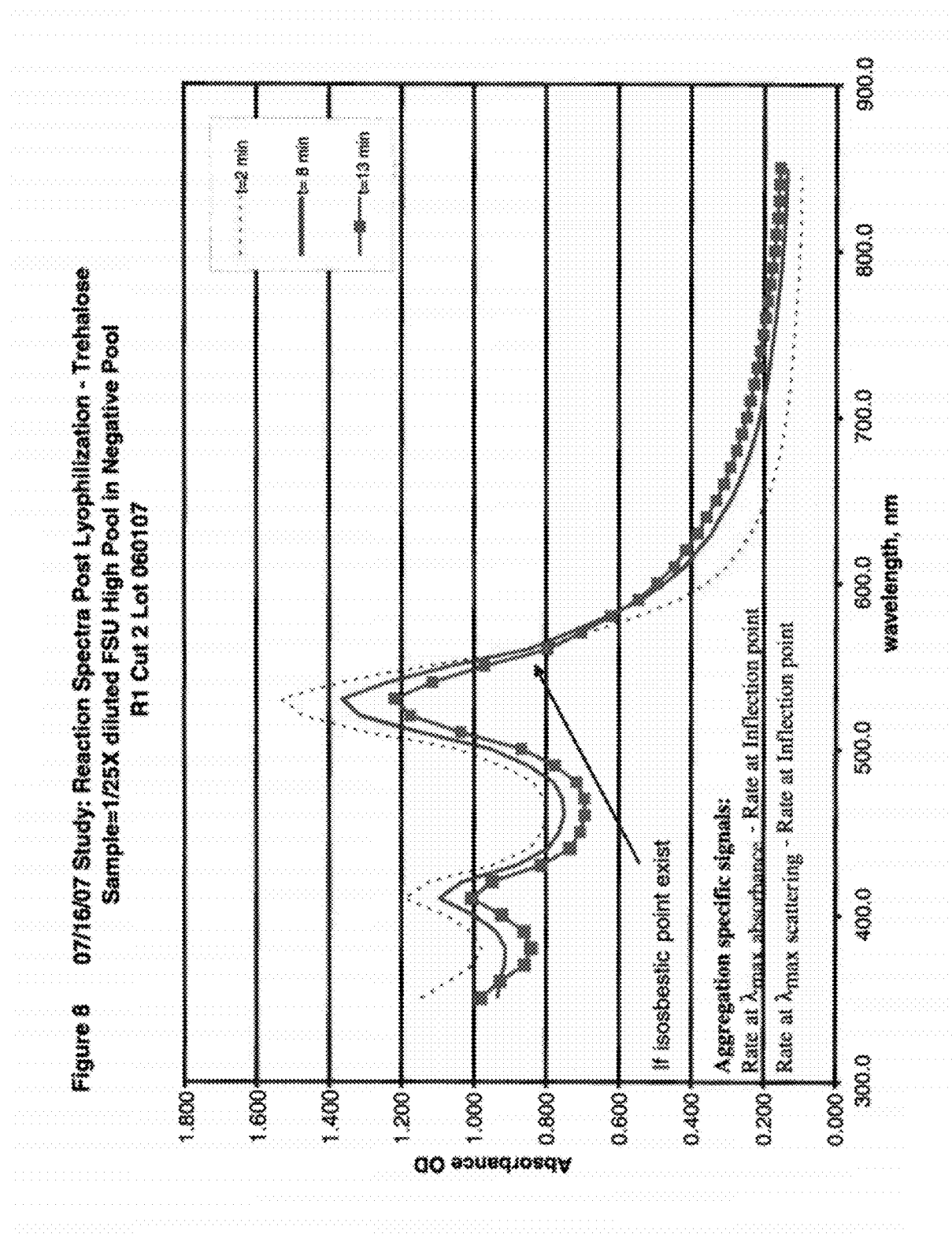
FIG. 8. Absorption spectra from different time points (2, 8, and 13 min) following incubation of gold-antibody conjugates with heartworm antigen illustrating the isosbestic point and rate calculations for aggregation specific signals.

Therefore, we developed a second logic to be used when there is very low reactivity between the analyte and conjugate. To quantify specific signals generated by agglutination, we used the isosbestic point as the reference wavelength. The rate calculations from the absorbance and scattering regions are shown in FIG. 8.

Figure 21:
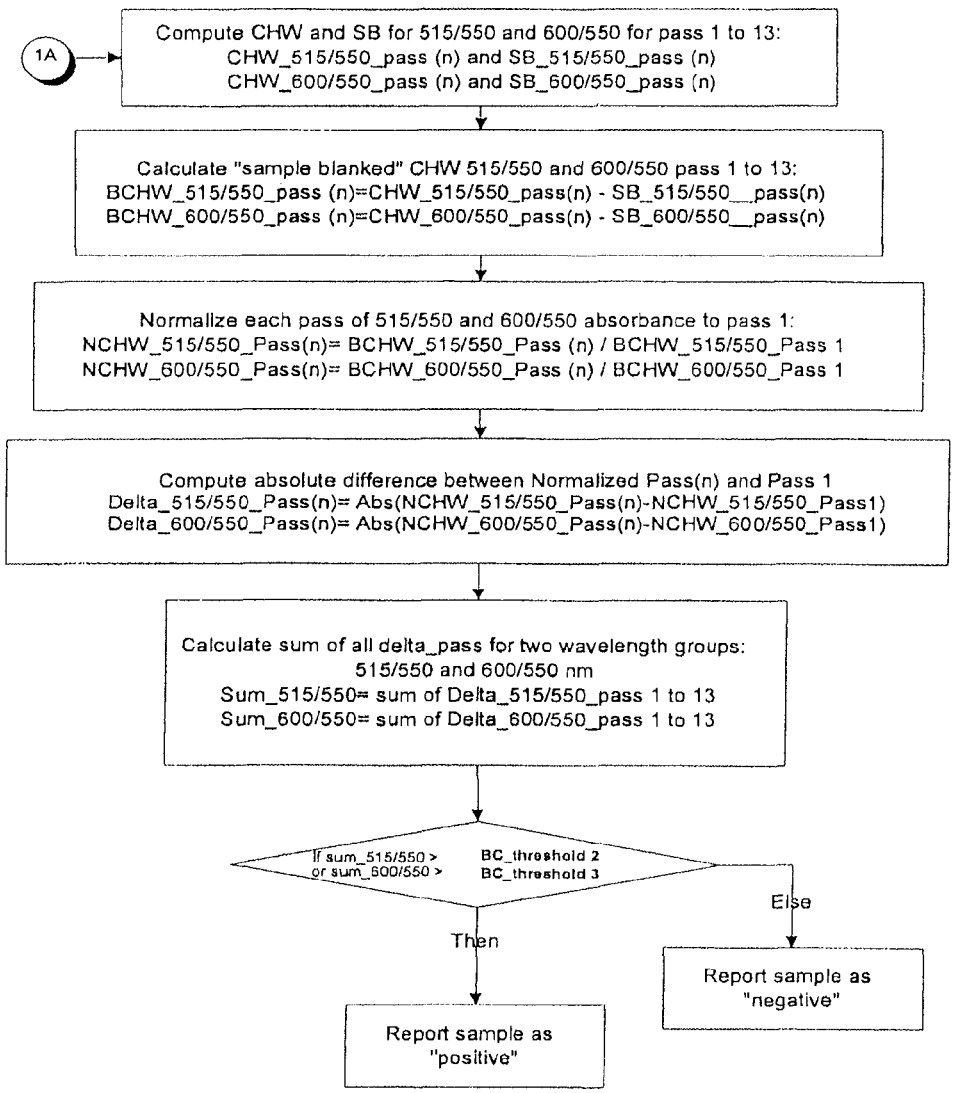
FIG. 21. Flow chart for the algorithm used in identifying positive samples when reactivity between analyte and conjugate is low (Logic #2).

This second logic (Logic #2) entails integrating negative and positive signals and is illustrated by the flow chart shown in FIG. 21.

In this example, there are 13 absorbance passes during the reaction. As described in FIG. 8, the isosbestic point is at 550 nm, and the absorbance and scattering wavelength region is represented by 515 nm and 600 nm, respectively.

Background sample colors are first blanked by subtracting the reaction rate of the sample buffer (SB) from the reaction rate of the canine heartworm sample (CHW) at each of the desired wavelengths (e.g. absorbance and scattering wavelengths). Each absorbance pass is then normalized to the first pass. Absolute delta change between each absorbance pass and the first pass is calculated. The final signal is then calculated by summing up all the absolute delta changes during the reaction.

Figure 9:
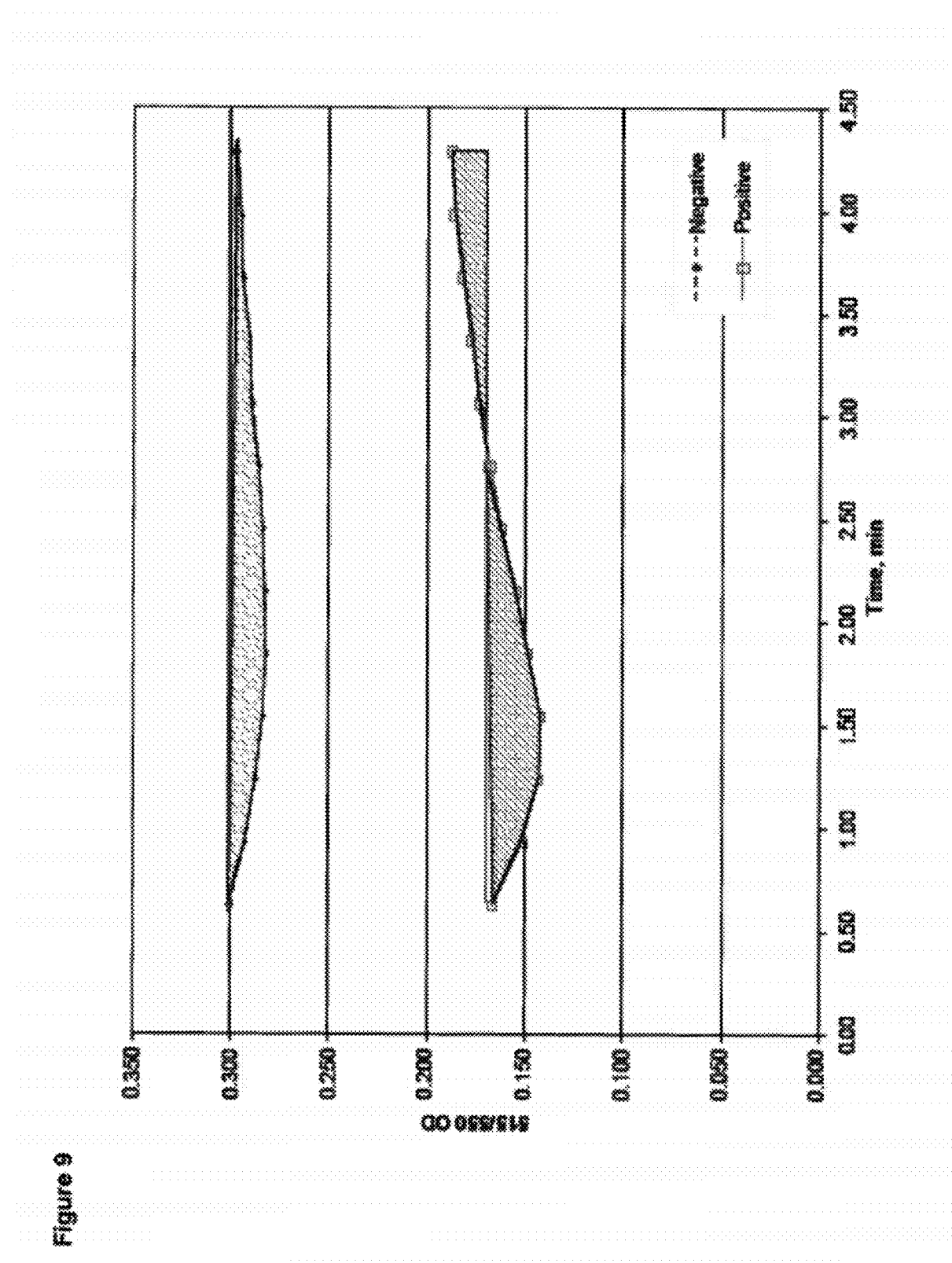
FIG. 9 illustrates signal integration according to logic #2 for a canine heartworm negative and positive sample.

The algorithm for 515/550 (absorbance wavelength/isosbestic point) is illustrated in FIG. 9 for a negative and positive sample. The shaded areas represent the maximum signal change obtained by any given pass. Thus, the second logic basically describes a simple way of integrating these shaded areas. Logic #2 may be used in conjunction with logic #1 or as a stand-alone logic. In very high reactivity conditions, the signals will be significantly amplified by normalization to the starting optical density (first pass).

Figure 10:
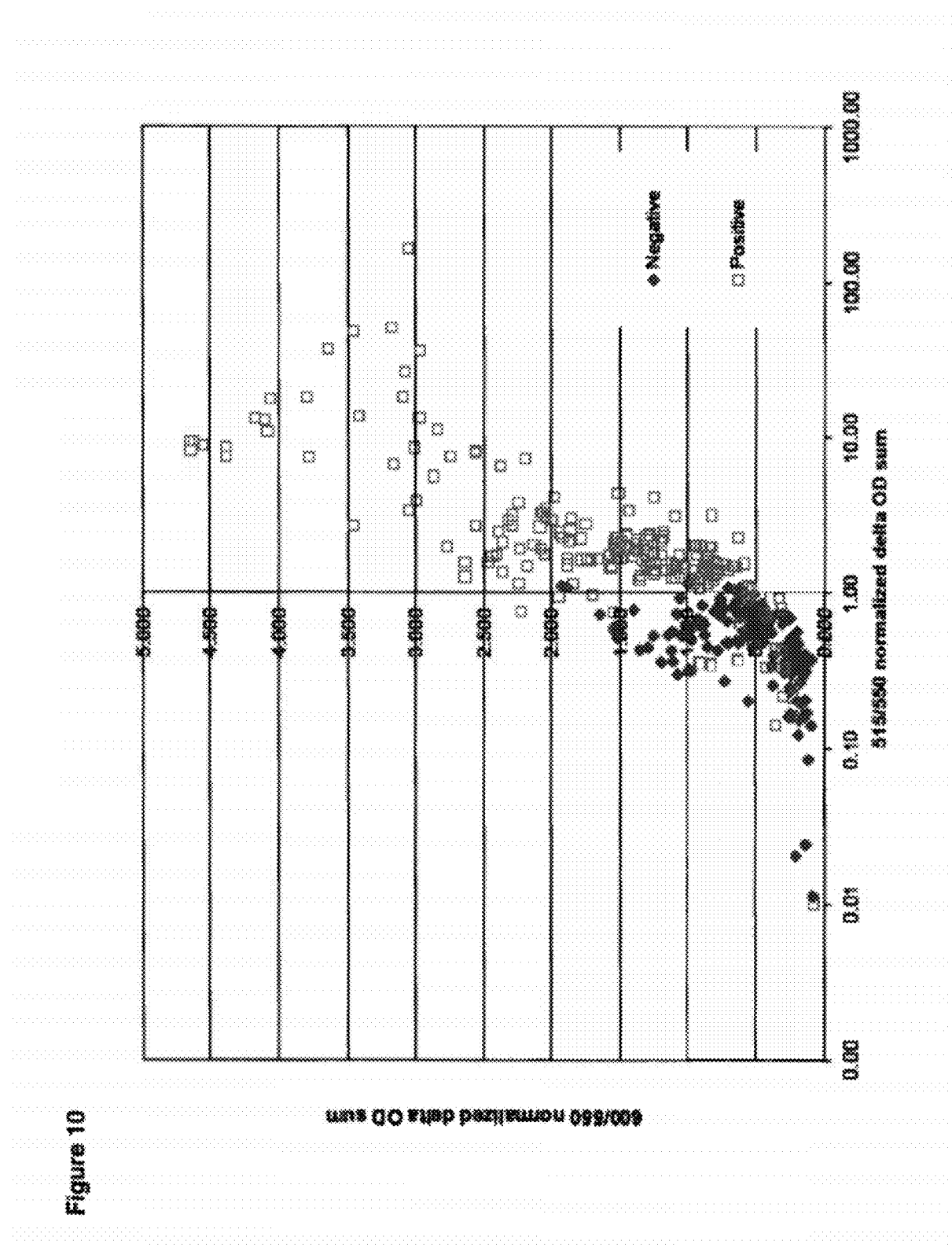
FIG. 10. Correlation between the normalized delta sum for reaction rates at the absorbance wavelength (515/550) and the normalized delta sum for reaction rates at the scattering wavelength (600/550) for negative and positive canine heartworm samples. The normalized delta sums were calculated according to logic #2.

The sensitivity of the assay is much improved by analyzing the absorbance spectra using logic #2. This improved sensitivity is illustrated by the correlation between the sum of the normalized deltas for reaction rates in the absorbance wavelength region (515/550) and the sum of the normalized deltas for reaction rates in the scattering wavelength region (600/550) for negative and positive canine heartworm samples (FIG. 10). Table 2 summarizes the number of samples identified as positive for CHW using logic #1. Table 3 summarizes the number of samples identified as positive for CHW using logic #2. A comparison of the results depicted in Tables 2 and 3 show that assay sensitivity is significantly improved when Logic #2 is used.

TABLE 2

Summary of samples identified as positive using Logic #1 algorithm

| | Run number | ID Positive? | % |
|---|---|---|---|
| Negative | 148 | 0 | 0.0% |
| Positive (5-15 worms) | 30 | 7 | 23.3% |
| Positive (20-30 worms) | 144 | 72 | 50.0% |
| Positive (31-50 worms) | 20 | 10 | 50.0% |

*weak conjugate reactivity

TABLE 3

Summary of samples identified as positive using Logic #2 algorithm

| | Run number | ID Positive? | % |
|---|---|---|---|
| Negative | 148 | 0 | 0.0% |
| Positive (5-15 worms) | 30 | 27 | 90.0% |
| Positive (20-30 worms) | 144 | 122 | 84.7% |
| Positive (31-50 worms) | 20 | 17 | 85.0% |

Figure 11:
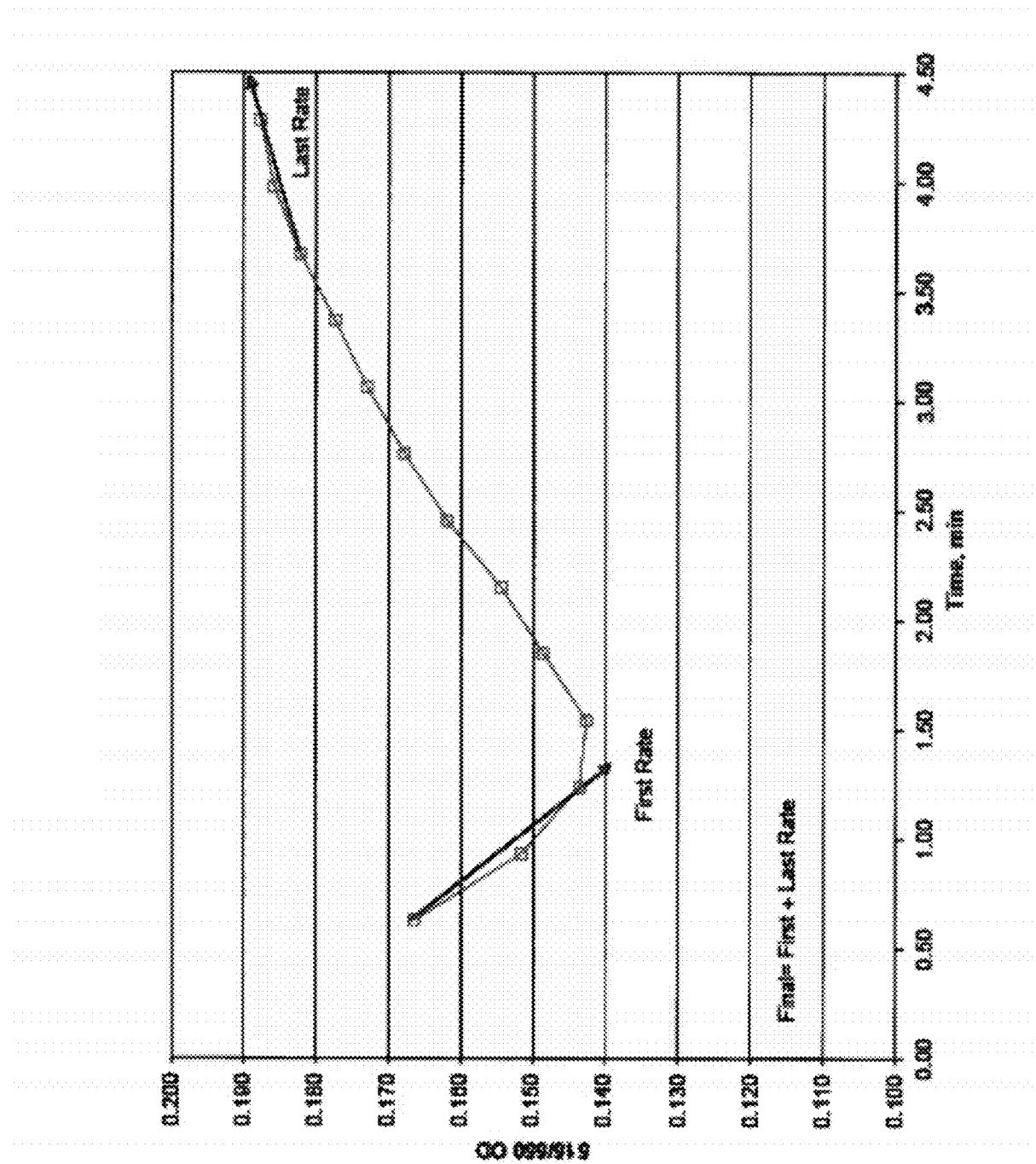
FIG. 11 illustrates an alternative method of analyzing reaction spectra using first and last rate sums.
Figure 12:
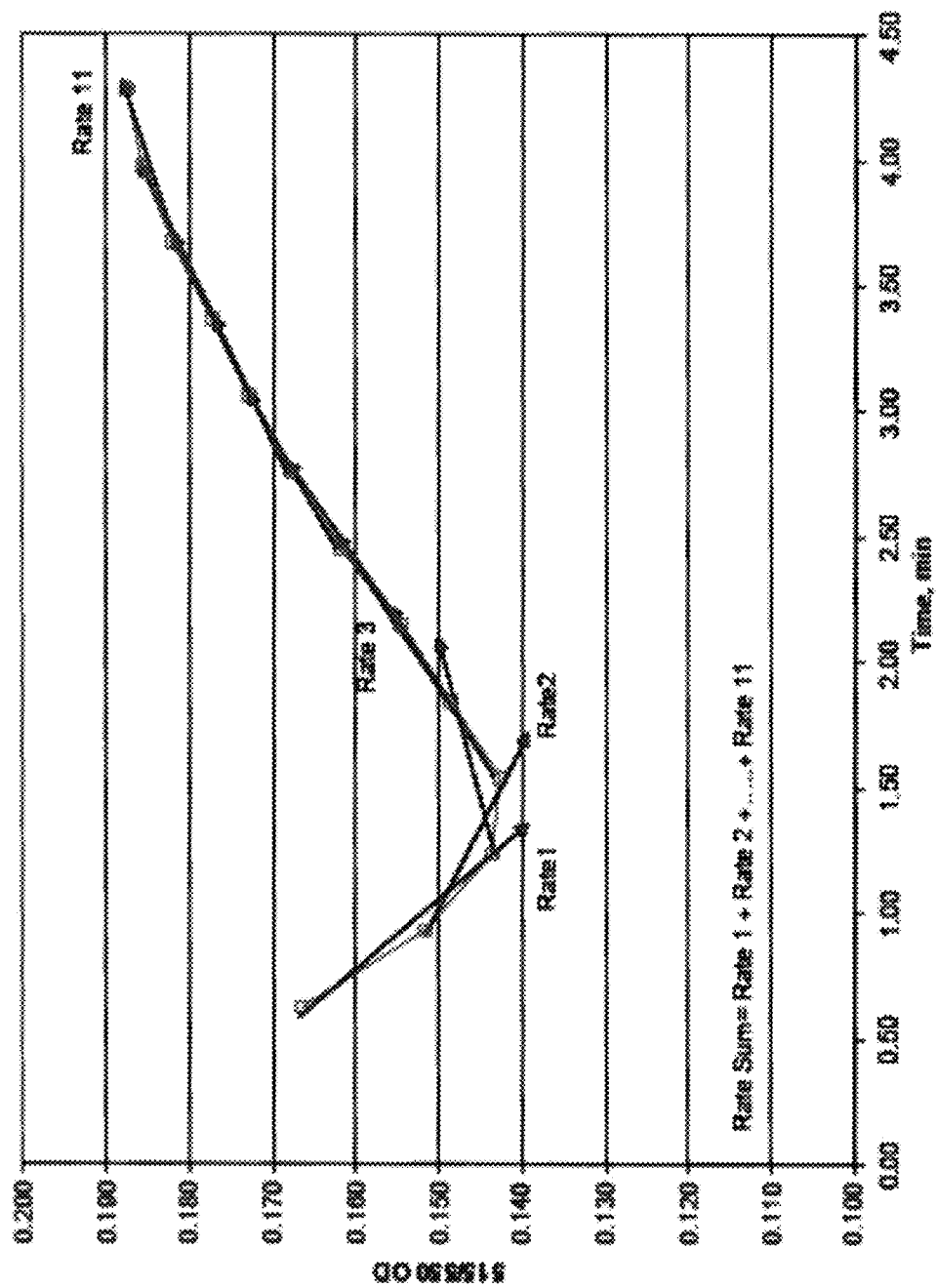
FIG. 12 illustrates a second alternative method of analyzing reaction spectra using the sum of interleaving rates.

FIGS. 11 and 12 illustrate two derivative ways of approximating the signals under the same signal integration scope. The method shown in FIG. 11 can be used when the reaction can be generally described by first and last rates. The method depicted in FIG. 12 traces and sums up interleaving rate changes of the reaction.

Example 4

Algorithm for Identifying Positive Samples when No Isosbestic Point can be Identified—Logic #3

Figure 22A:
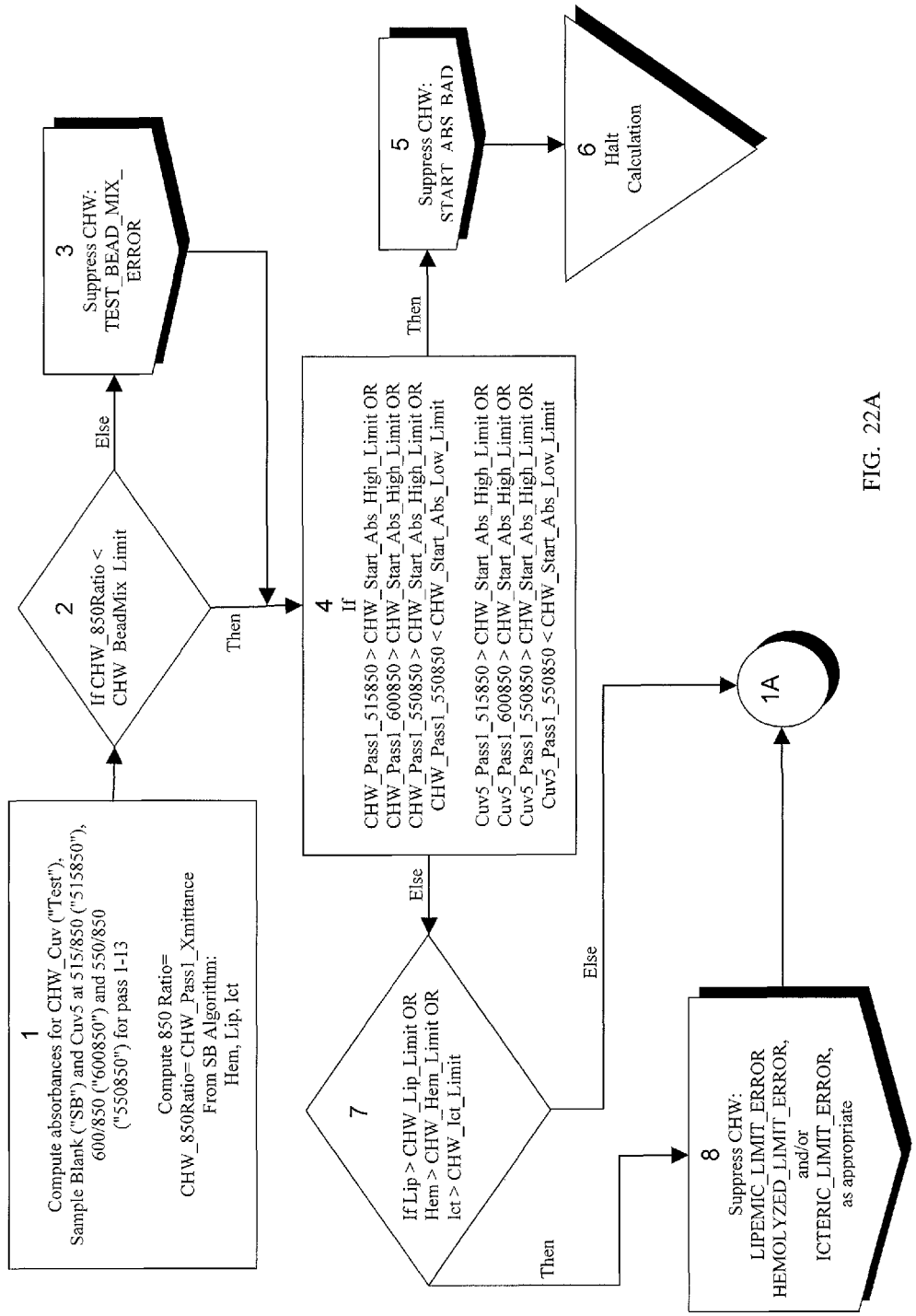
FIG. 22. Flow chart for the algorithm used in identifying positive samples when no isosbestic point can be identified (Logic #3). A. Steps of algorithm providing for assessment of the integrity of the reagents as well as other parameters of the reaction to prevent inaccurate absorbance measurements leading to false positives and false negatives. B. Steps of algorithm for calculating absorbance ratio and rate for determining the presence or absence of analyte.

This example provides a qualitative algorithm for detecting the presence of analyte (e.g. canine heartworm) in a sample using gold nanoparticle conjugates. This algorithm is particularly useful when an isosbestic point cannot be determined from the spectra and utilized to calculate reaction rate changes as described in Logic #2 (Example 3). The algorithm in this Example utilizes two key characteristics found in spectra resulting from colloidal gold agglutination. As shown in FIG. 13, the absorbance peak broadens and the absorbance maximum (lambda max) decreases over time in the presence of analyte (e.g. a positive reaction). Thus, measurements of absorbance rate and/or absorbance peak broadness reflect the specific binding of gold nanoparticle conjugates with analytes in a sample. This algorithm also provides several measurements for assessing the integrity of the reagents as well as other parameters of the reaction to prevent inaccurate absorbance measurements leading to false positives and false negatives. A flow chart depicting the full algorithm is shown in FIGS. 22A and B.

In this algorithm, absorbance values are determined in the absorbance region (e.g. 515 nm) and the scattering region (e.g. 600 nm) of the spectra relative to a reference wavelength (e.g. 850 nm) for test samples and control samples (e.g. sample blanks, sample buffer only). The maximum absorbance value or absorbance peak is also determined (550 nm in this Example) for each of the samples. Preferably the absorbance is determined at wavelengths which fall within the ascending and descending phases of the absorbance peak. The absorbance values at each of the wavelengths may be obtained at multiple time points during the reaction.

The dissolution of the gold nanoparticle conjugates (i.e. bead dissolution) is verified by measuring transmittance at 850 nm at an initial time point of the reaction. In significant agglutination reaction, 850 nm absorbance can be elevated as shown in FIG. 13, which can reduce transmittance at 850 nm in test samples. Therefore, the initial value of transmittance at 850 nm is compared to a pre-determined limit value to verify adequate bead dissolution. The pre-determined limit value may be based on 850 nm transmittance values obtained from several reactions. For example, the lowest 850 nm transmittance value from recent studies was about 0.6. For the detection of canine heartworm antigen with gold nanoparticle-antibody conjugates, we set the bead dissolution limit (CHW_BeadMix_limit) at 0.5, which is much lower than typical bead dissolution limits for other analytes. If a transmittance value at 850 nm obtained in a test sample is higher than the bead dissolution limit (e.g. 0.5), then the algorithm returns a "Test Bead Mix Error" to reflect inadequate dissolution of the gold nanoparticle conjugate. These initial calculations of the algorithm are shown as steps 1 to 3 in the flow chart depicted in FIG. 22A.

To ensure an adequate concentration of gold particle conjugates is present in the reaction mixture, the absorbance values at the measured wavelengths (e.g. in the absorbance region, scattering region, and $\lambda_{max}$) obtained at an initial time point in the reaction (first pass) may be compared to pre-determined high and low absorbance limits. The high absorbance limit may be based on the maximum detection limit of the instrument used to measure absorbance. In this Example, we used a limit of 3.0, which is the photometer limit of the analyzer used to acquire absorbance spectra, as the high absorbance limits (start_abs_high_limits) for 515/850, 550/850 and 600/850. A low starting absorbance limit at $\lambda_{max}$ may be based on a minimum level of detection of the instrument acquiring the absorbance spectra. For example, a low absorbance limit at 550 nm (close to lambda max) is set at 0.5 to ensure minimum conjugate concentration. If the initial absorbance values at any of the measured wavelengths (e.g. in the absorbance region, scattering region, and $\lambda_{max}$) exceeds the starting high absorbance limit, the algorithm returns a "Starting Absorbance Bad" error message to indicate the conjugate concentration is too high. Similarly, if the initial absorbance reading at $\lambda_{max}$ is less than the starting low absorbance limit, then the algorithm will return the same error message indicating that the conjugate concentration is too low. These measurements are illustrated as steps 4 to 6 in the flow chart shown in FIG. 22A.

Additional limits may be determined to eliminate samples that have a high concentration of one or more components that may interfere with absorbance readings. For example, calculations based on the absorbance of sample blanks may be used to determine such limits. Initial absorbance measurements at wavelengths in the absorbance and scattering regions obtained for a control sample (e.g. sample only, sample blank) may be compared to one or more of these limits. If the initial absorbance measurements exceed these pre-determined limits, then the algorithm will return an error message indicating the sample contains a high concentration of one or more of these interfering components (see step 7 in flow chart in FIG. 22A).

Ratio Calculation

Figure 14A:
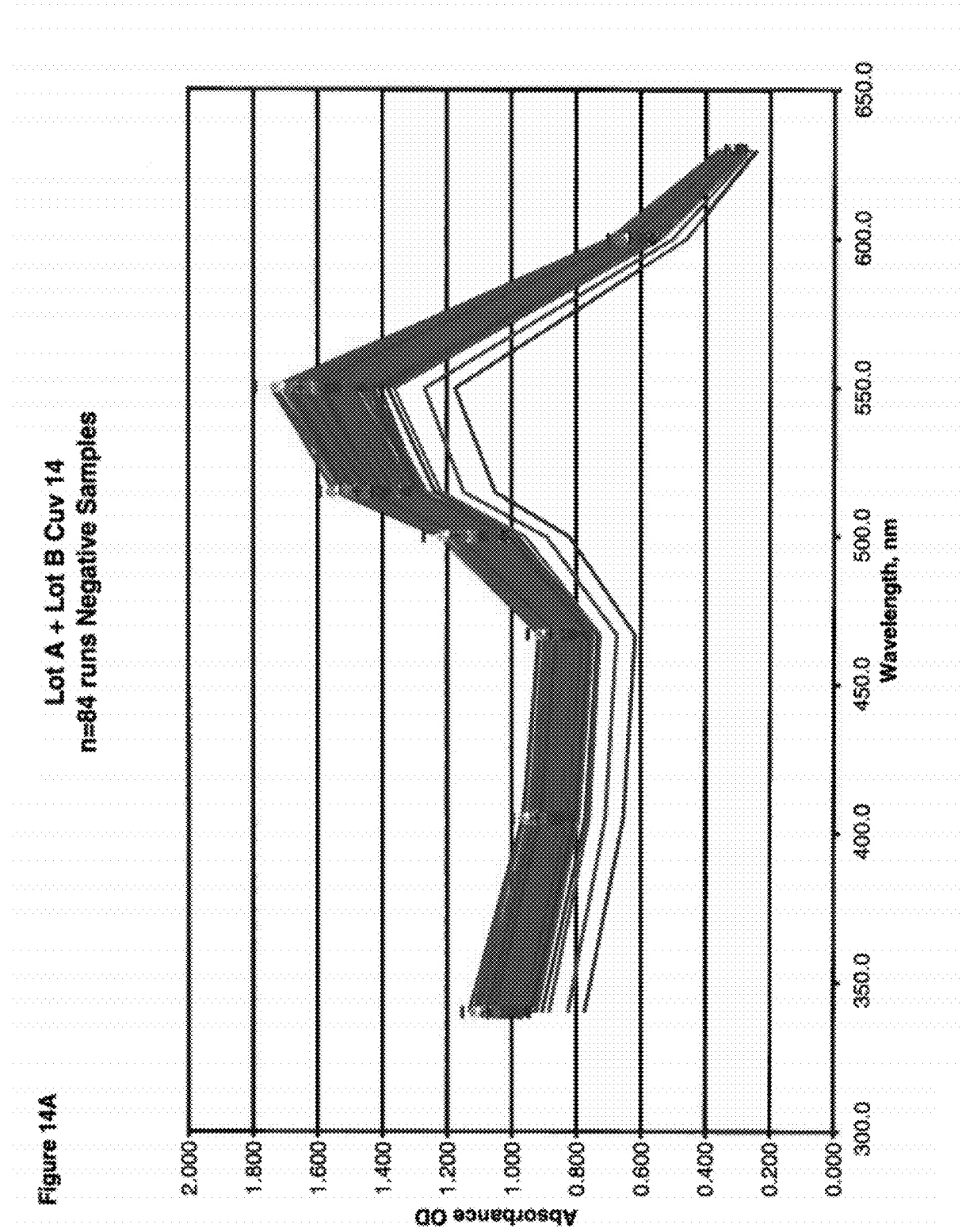
FIG. 14. A. Absorbance spectra for 84 different samples negative for canine heartworm. B. Normalized absorbance spectra for the same samples in A. The absorbance at each wavelength was normalized to the absorbance at 550 nm ($\lambda_{max}$).
Figure 14B:
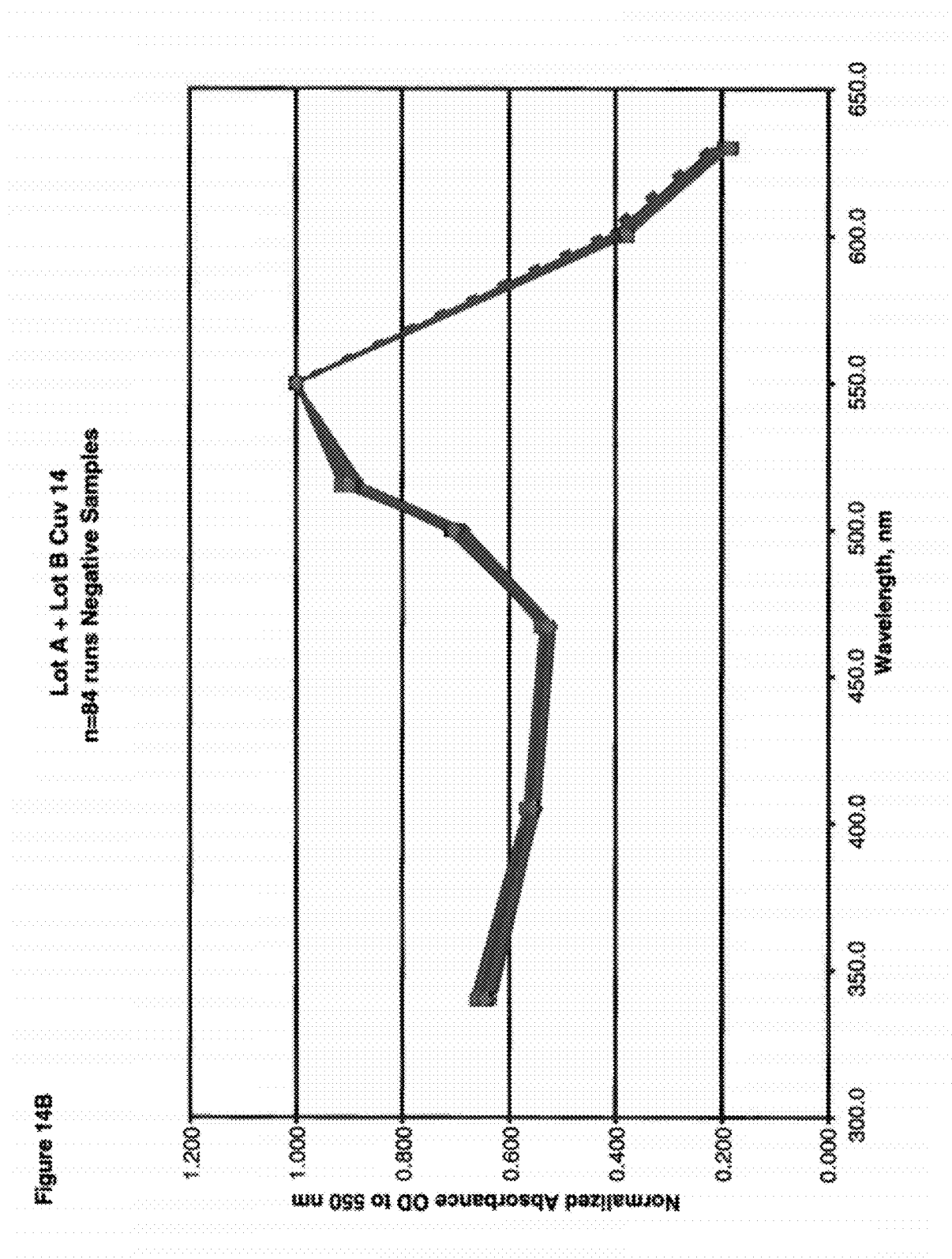

As shown in FIG. 14A, we observed an apparent peak height variation among 84 different samples negative for canine heartworm. This variation may be due to dispensing error, bead mass loss, or non-specific adsorption/precipitation to sample components. To determine whether the absorbance variation is due to false agglutination, we normalized absorbance ODs of each run to 550 nm ($\lambda_{max}$). The results are illustrated in FIG. 14B. The normalized spectra exhibited excellent consistency among negative samples, suggesting no peak broadening or agglutination occurs in these negative samples.

Figure 15B:
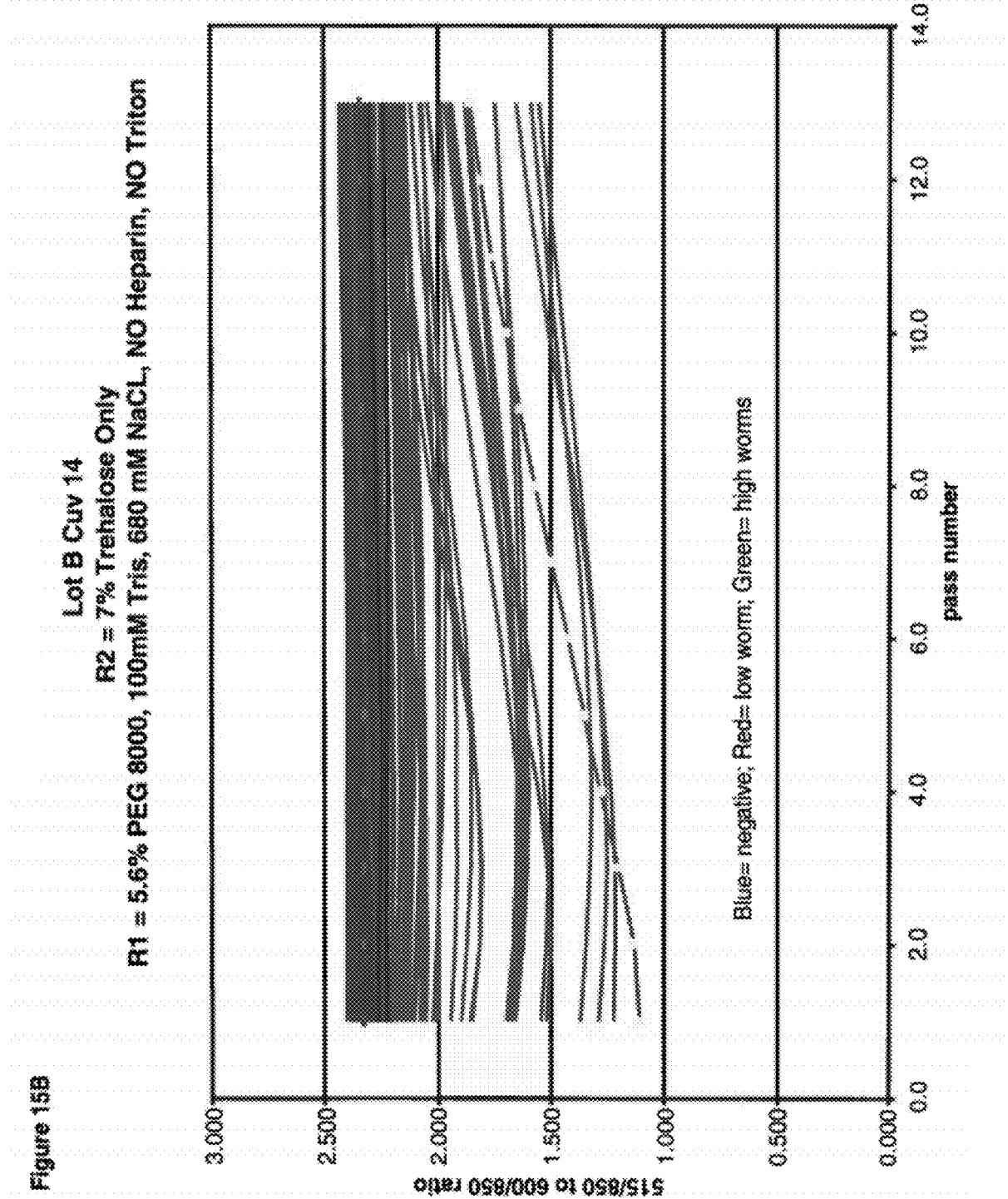
FIG. 15. A. Normalized absorbance spectra for various heartworm antigen concentrations. The absorbance at each wavelength was normalized to the absorbance at 550 nm ($\lambda_{max}$). B. Ratio of absorbance at 515 nm to absorbance at 600 nm is plotted versus reaction time (pass number) for samples containing various heartworm antigen concentrations.

FIG. 15A illustrates normalized absorbance spectra for various heartworm antigen concentrations. The normalized absorbance values at 515 nm and 600 nm showed opposite trending as antigen concentration increased. Specifically, the absorbance at 515 nm decreased with increasing antigen concentration, while the absorbance at 600 nm increased. Thus, the wavelength ratio between 515 nm and 600 nm decreases in the presence of canine heartworm (CHW) antigen. FIG. 15B shows the 515/600 ratio over time for samples containing various concentrations of CHW antigen. The ratio is most sensitive in the beginning of the reaction. Therefore, an average of the first five passes of the ratio between 515 and 600 nm may be used to assess conjugate agglutination and thus, presence of antigen in sample. Alternatively, the ratio of the absorbance at 600 nm to the absorbance at 515 nm may be used. In this case, the wavelength ratio will increase in the presence of CHW antigen.

The next series of steps in the algorithm entails the calculation of the ratio of the absorbance at a wavelength in the scattering region (e.g. 600 nm) to an absorbance at a wavelength in the absorbance region (e.g. 515 nm) and the comparison of this ratio to a cut-off value or threshold value. The ratio cut-off value may be established by a population of negative samples or a diluted antigen (worm extract) control, which represents the assay signal sensitivity cut-off. If the calculated ratio for a test sample exceeds the ratio cut-off value, the algorithm will report a "Positive" result (see steps 9-13 in the flow chart shown in FIG. 22B).

Figure 16A:
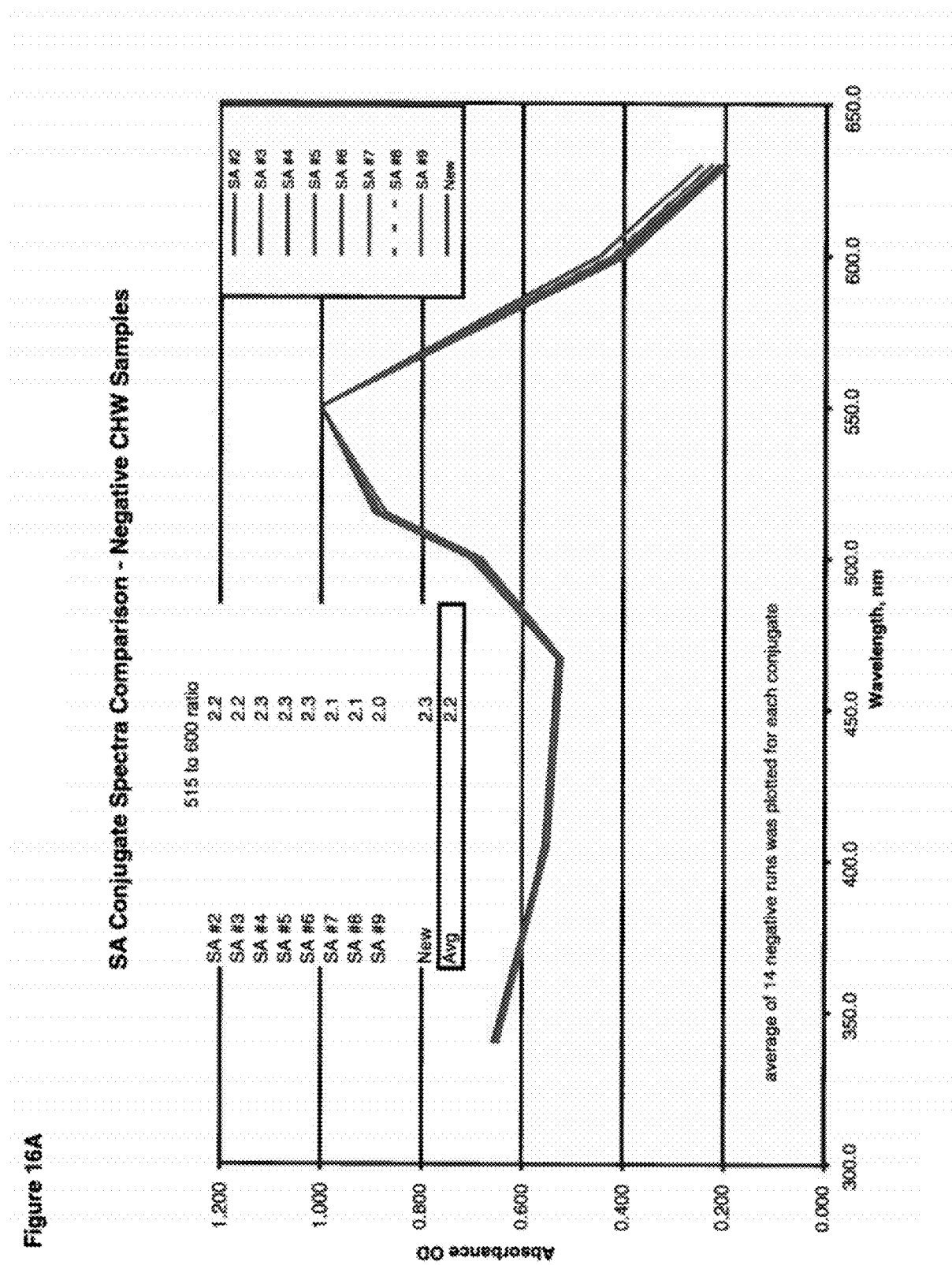
FIG. 16. A. Absorbance spectra for nine different gold nanoparticle conjugates mixed with samples negative for canine heartworm. The ratio of absorbance at 515 nm to the absorbance at 600 nm for each of the conjugates is shown in the inset. B. Ratio of absorbance at 515 nm to absorbance at 600 nm is plotted versus heartworm antigen concentration (expressed as dilution ratio). At high antigen concentrations (1:100), the ratio begins to plateau.

Error traps for erroneous ratio results may also be established. In theory, the wavelength ratio (515 nm/600 nm) should not be greater than native conjugate reagents. FIG. 16A compares nine different gold nanoparticle conjugate batches from SA Scientific. The 515 nm/600 nm ratio ranged from 2.0 to 2.3. Therefore, in this Example, the wavelength ratio high limit (CHW_Ratio_High_Limit) is set to 2.5. If the 600 nm/515 nm ratio is used instead of the 515 nm/600 nm ratio, a similar analysis to that described above can be used to establish the wavelength ratio low limit.

The low ratio limit for the 515 nm/600 nm ratio may be based on ratio values obtained at very high antigen concentrations. For Example, FIG. 16B illustrates the dose response of the absorbance ratio at different worm extract dilutions. At extremely elevated antigen concentration (1:100 dilution), the ratio generally reached a plateau. Therefore, we set the wavelength ratio low limit (CHW_Ratio_Low_Limit) to 1.0. Again, if the ratio of absorbance at 600 nm to the absorbance at 515 nm is used, analysis of the dose-response data can be used to establish the wavelength ratio high limit. If the wavelength ratio determined for the test sample is greater than the wavelength ratio high limit or less than the wavelength ratio low limit, then the algorithm will return a ratio error message. See steps 10 and 11 in the flow chart shown in FIG. 22B.

Rate Calculation

Figure 17A:
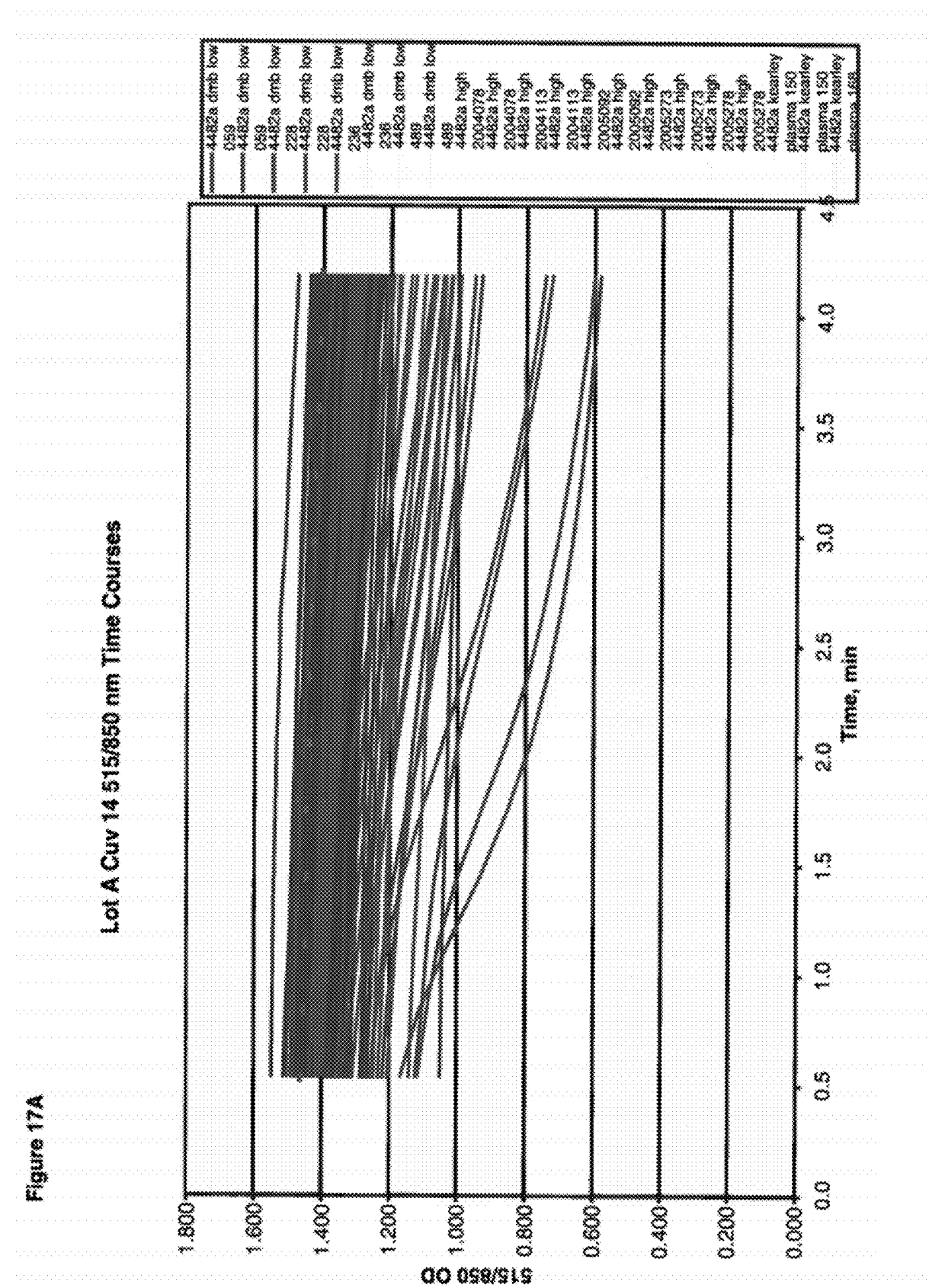
FIG. 17. Plot of change in absorbance of gold nanoparticle conjugates versus reaction time at 515 nm (A) or 600 nm (B) in the presence of different concentrations of heartworm antigen. Blue lines represent negative plasma samples, red lines represent low antigen concentration, and green lines represent high antigen concentration.
Figure 17B:
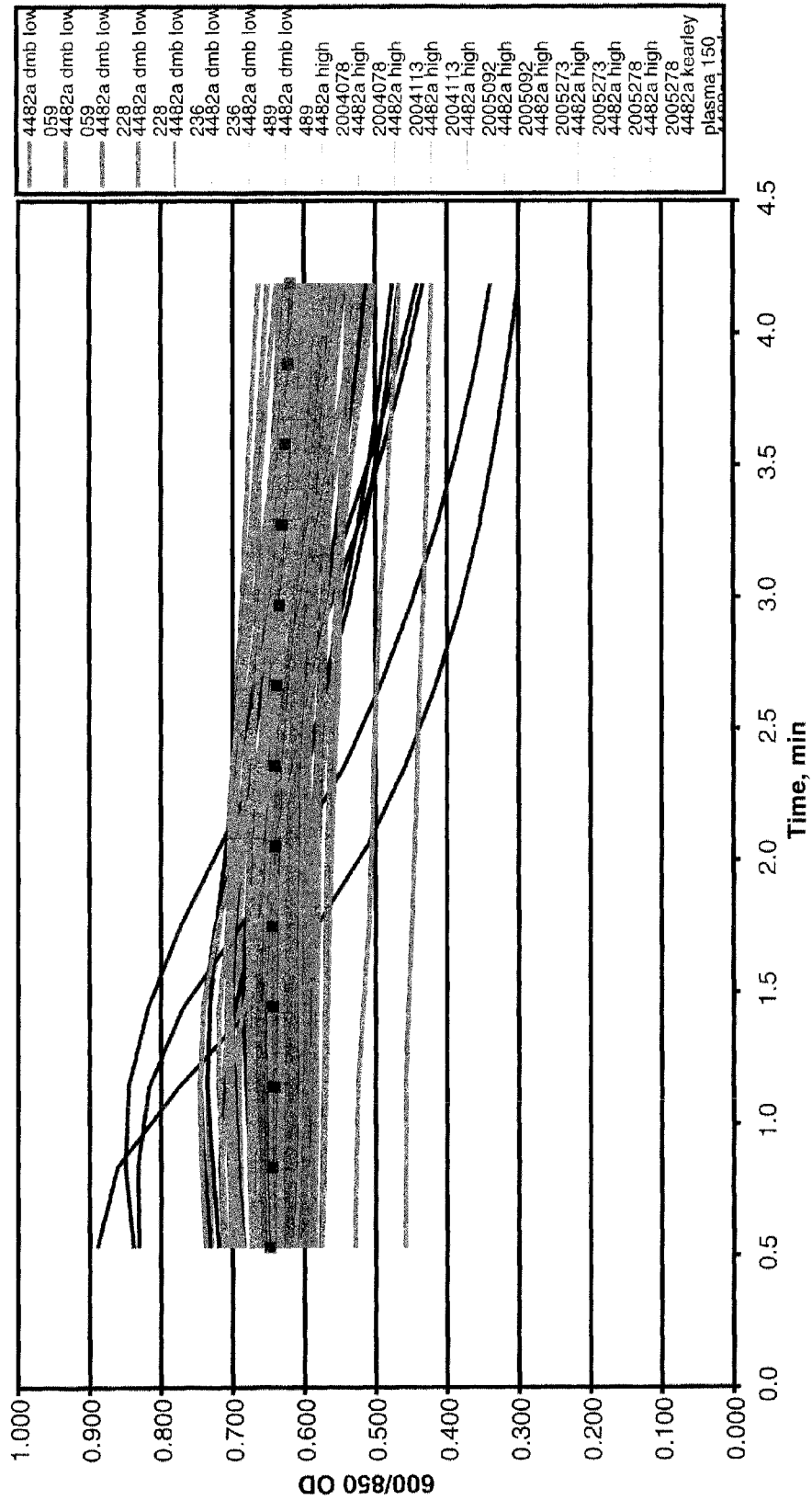

The absorbance rate or reaction rate (e.g. change in absorbance over reaction time) at a wavelength in the absorbance region (e.g. 515 nm) and in the scattering region (e.g. 600 nm) as described above for Logics 1 and 2 may also be used in conjunction with the ratio calculation to assess conjugate agglutination, and thus the presence of antigen. Absorbance time courses for 515 nm and 600 nm are illustrated in FIGS. 17A and B, respectively. Absorbance generally decreases over time due to the centrifugal force applied to the rotor in which the absorbance of the samples is measured. The reaction linearity worsens at highly elevated antigen concentrations (green lines). The measured negative absorbance rate values may be converted to positive values by multiplying the values by "−1".

Figure 22B:
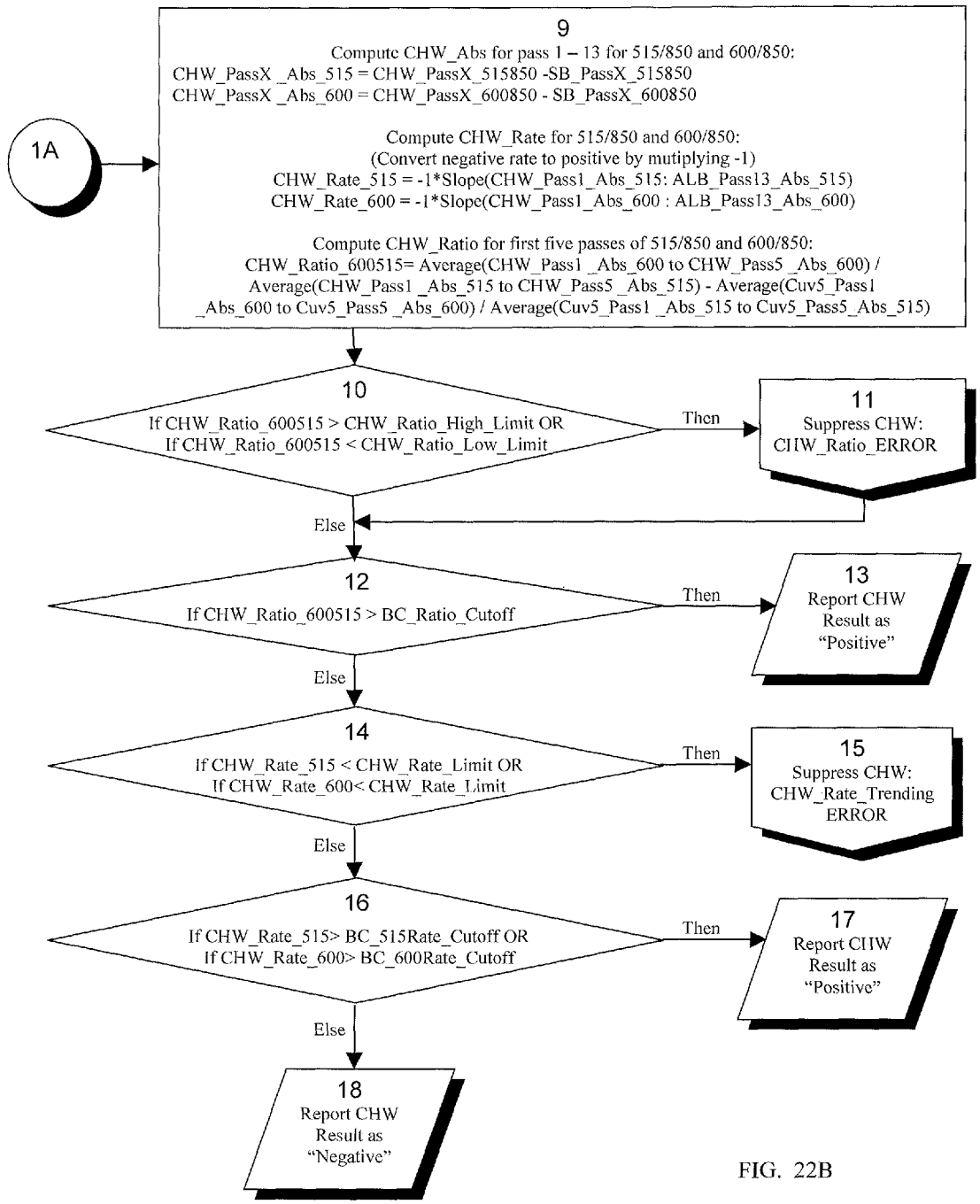

A final series of steps in the algorithm utilizes reaction rates at each of the wavelengths to determine the presence of antigen (see steps 14-18 in FIG. 22B). The reaction rates are determined by calculating the slopes between pass 1 to 13 for both 515 nm and 600 nm. A dynamic window switching could be employed for identifying the most linear part of the reaction. FIG. 18 illustrates the dose response comparison between the two wavelengths at various heartworm extract dilutions.

Cut-off rates or threshold rates for each wavelength may be established by a population of negative samples or diluted worm extract controls, which represent the assay signal sensitivity cut-off. When using negative reaction rates, if the reaction rate is below the cut-off rates of either wavelength, the algorithm will report a "Positive" result. Alternatively, when using positive reaction rates, if the reaction rate is greater than the cut-off rates of either wavelength, the algorithm will report a "Positive" result.

A general reaction trending can be verified by establishing rate limits at each wavelength. For the SA gold nanoparticle conjugate, we set the rate limit (CHW_Rate_Limit) at 0.

Addition of Optical Blank to Minimize Instrument-to-Instrument Variation

Figure 19A:
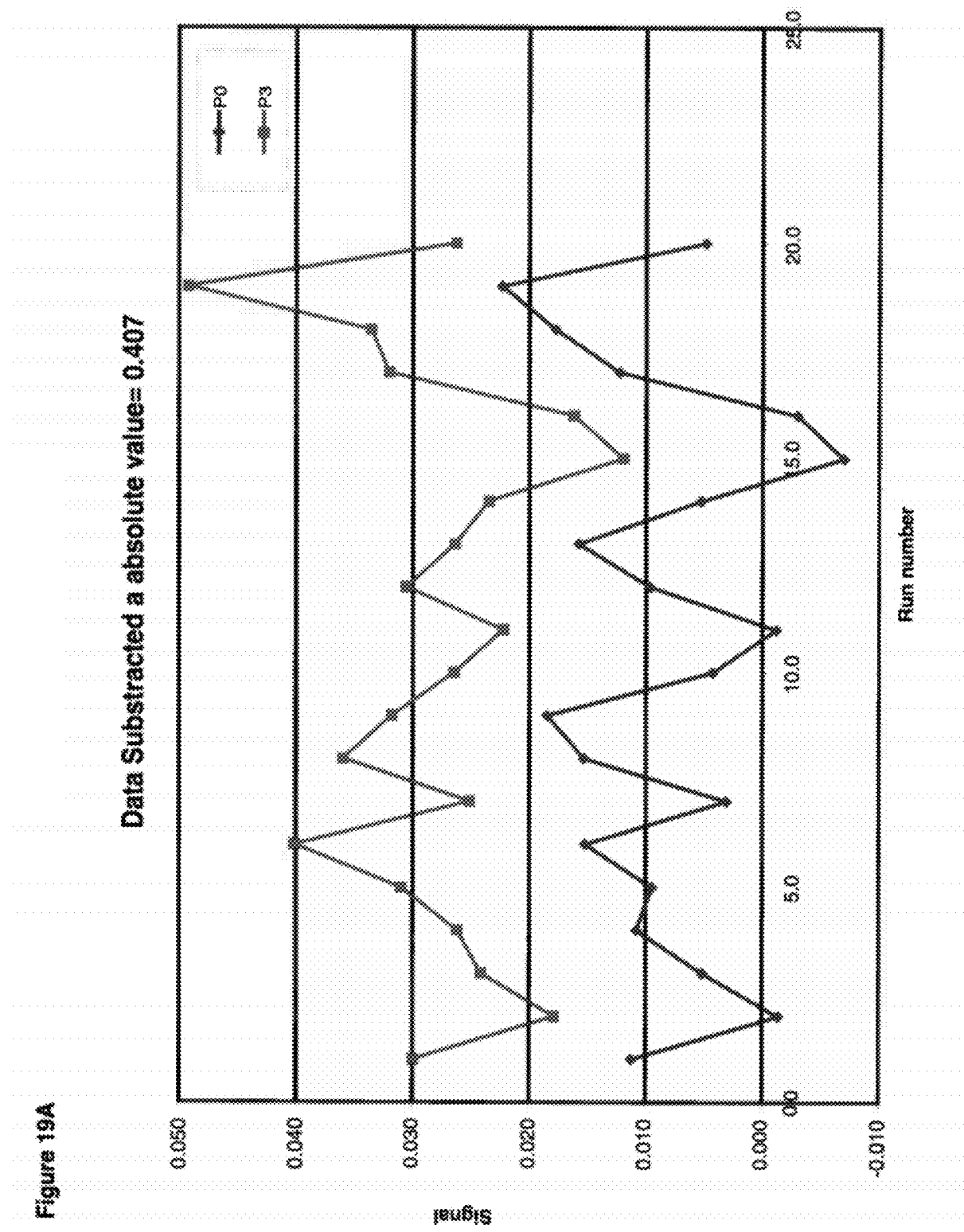
FIG. 19. A. Absorbance signal of gold nanoparticle conjugates in the presence of two different antigen-containing samples (P0 and P3) measured on twenty different analyzers. Each data point represents a different analyzer. B. Absorbance signal as shown in A corrected for the absorbance of an optical blank (gold nanoparticle conjugates alone-no sample).

Although the wavelength ratio measurement described above provides exquisite sensitivity for detecting the presence of antigen in sample, it was also very sensitive to any subtle optical difference between analyzers. FIG. 19A illustrates the signals (e.g. adjusted wavelength ratios) obtained for two different antigen-containing samples (P0 and P3) from twenty different analyzers. To ensure a valid comparison, the wavelength ratios were adjusted by subtracting an absolute value of 0.407, which was the average value obtained from the optical cuvette across the different analyzers. The object of the experiment was to demonstrate assay precision using a pre-determined offset value that does not change from instrument to instrument in comparison to the true measurement value from the optical cuvette tested on each instrument. For each sample, each data point represents a different analyzer. The results show an obvious systematic bias due to instrument variations.

Figure 19B:
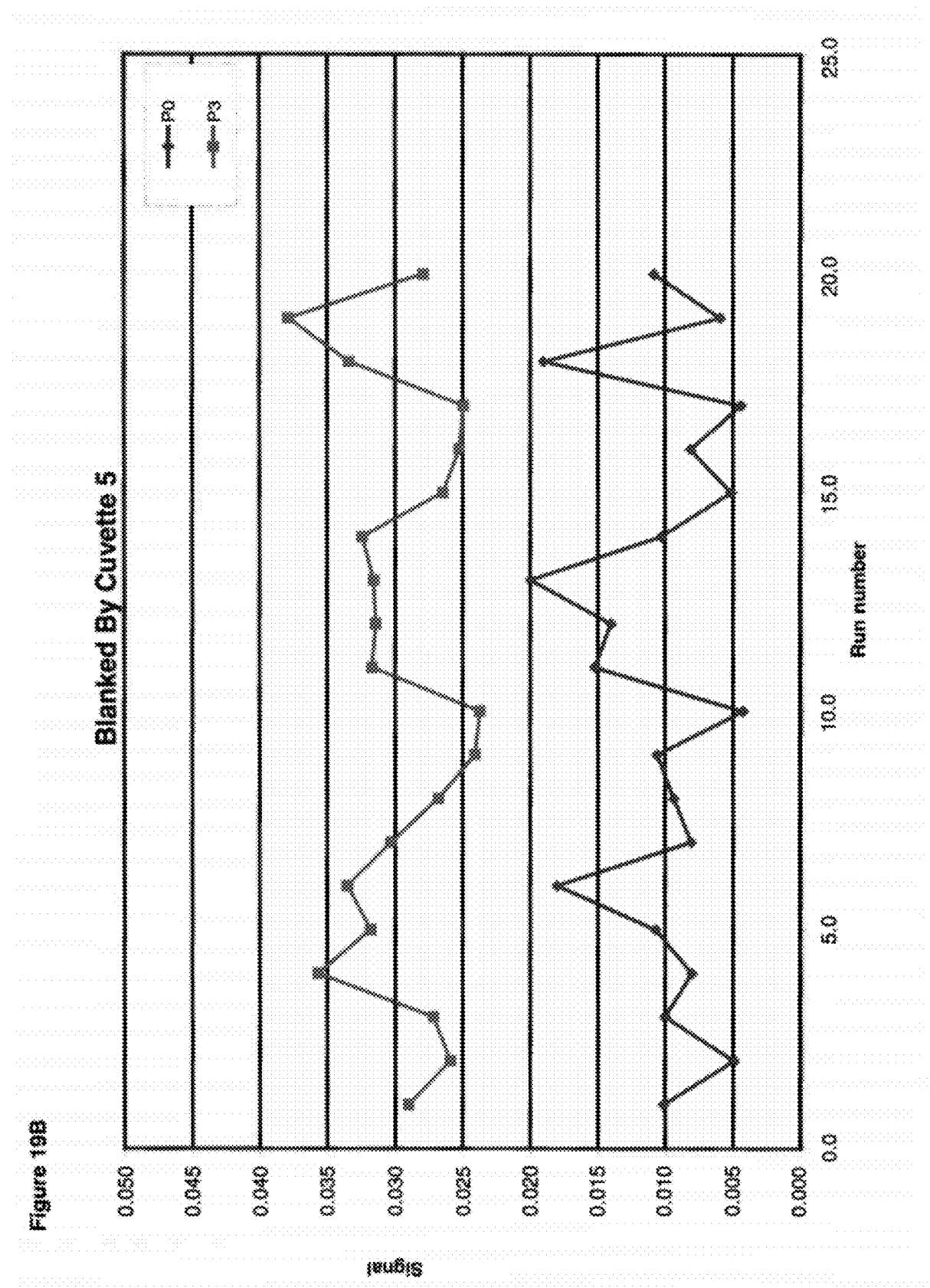

To correct this variation, we used the conjugate bead alone as an optical blank (Cuv 5) to preserve the conjugate wavelength ratio, which eliminates the variation between different instruments. FIG. 19B shows the results on twenty instruments when the optical blank conjugate bead was used. It is clear from the results that use of an optical blank improves the precision and sensitivity of the assay.

Table 4 below summarizes the limit values for the different error traps described above as well as the bar-code (BC) equations used in the Logic #3 algorithm for detecting canine heartworm in biological samples with gold nanoparticle conjugated antibodies.

TABLE 4

Error Trap limits and Bar-code equations for the Logic #3 algorithm

| | |
|---|---|
| CHW_Start_Abs_High_Limit | 3 |
| CHW_Start_Abs_Low_Limit | 0.5 |
| CHW_Lip_Limit | 4000 (tentative) |
| CHW_Hem_Limit | 2000 (tentative) |
| CHW_Ict_Limit | 40 (tentative) |
| CHW_Ratio_High_Limit | 0.61 |
| CHW_Ratio_Low_Limit | 0 |
| CHW_Rate_Limit | 0 |
| (Rate should be always greater than 0) | |

| BC equation | Range | Equations |
|---|---|---|
| CHW_Ratio_Cutoff | 0 to 0.16 | 0.00162 * X |
| CHW_515Rate_cut_off | 0.01 to 0.11 | 0.001 * X + 0.01 |
| CHW_600Rate_cut_off | 0.01 to 0.11 | 0.001 * X + 0.01 |

The complete Logic #3 algorithm is illustrated by the flow chart in FIGS. 22 A and B.

It is understood that the disclosed invention is not limited to the particular methodology, protocols and materials described as these may vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for determining the presence or absence of a complex of a first reagent and a second reagent in a mixture comprising
    determining a first reaction rate change at a first wavelength and a second reaction rate change at a second wavelength upon mixing the first reagent with the second reagent, wherein the first reagent or the second reagent is conjugated to a metal nanoparticle or nanoshell,
    wherein the first wavelength is within an absorbance wavelength region and the second wavelength is within an absorbance wavelength region or scattering wavelength region of the absorption spectrum for the metal nanoparticle or nanoshell, and
    wherein the first reaction rate change and the second reaction rate change are indicative of the presence or absence of the complex of the first reagent and the second reagent.

2. The method of claim 1,
    wherein the first wavelength and the second wavelength are within the absorbance wavelength region of the absorption spectrum for the metal nanoparticle or nanoshell.

3. The method of claim 1,
    wherein the first wavelength is within the absorbance wavelength region of the absorption spectrum for the metal nanoparticle or nanoshell and the second wavelength is within a scattering wavelength region of the absorption spectrum for the metal nanoparticle or nanoshell.

4. The method of claim 1, comprising
    determining for a first time point a first reaction rate change at a first wavelength and a second reaction rate change at a second wavelength,
    determining for a second time point a third reaction rate change at the first wavelength and a fourth reaction rate change at the second wavelength,
    wherein the first and second wavelength are within the absorbance wavelength region of the absorption spectrum for the metal nanoparticle or nanoshell, and
    wherein the first, second, third, and fourth reaction rate change are indicative of the presence or absence of the complex.

5. The method of claim 4, wherein the first time point is within an initial period of mixing the first reagent with the second reagent and wherein the second time point is within a last period of mixing the first reagent with the second reagent.

6. The method of claim 1, comprising
    determining for a first time point a first reaction rate change at a first wavelength and a second reaction rate change at a second wavelength,
    determining for a second time point a third reaction rate change at the first wavelength and a fourth reaction rate change at the second wavelength,
    wherein the first wavelength is within the absorbance wavelength region of the absorption spectrum for the metal nanoparticle or nanoshell and the second wavelength is within the scattering wavelength region of the absorption spectrum for the metal nanoparticle or nanoshell, and
    wherein the first, second, third, and fourth reaction rate change are indicative of the presence or absence of the complex.

7. The method of claim 6, wherein the sum of first and second reaction rate changes is compared to a first predetermined threshold value.

8. The method of claim 6, wherein the ratio of the sum of the first and second reaction rate changes versus the sum of the third and fourth reaction rate changes is compared to a second predetermined threshold value.

9. The method of claim 6, wherein the sum of the first and second reaction rate changes is compared to a first predetermined threshold value, wherein the ratio of the sum of the first and second reaction rate changes versus the sum of the third and fourth reaction rate changes is compared to a second predetermined threshold value, and wherein the comparison to the first predetermined threshold value and the second predetermined threshold value are indicative of the presence or absence of the complex.

10. The method of claim 6, wherein the first time point is within an initial period of mixing the first reagent with the second reagent and wherein the second time point is within a last period of mixing the first reagent with the second reagent.

11. The method of claim 6, wherein the first time point is 0.5, 1, 2, 3, 4, or 5 minutes upon mixing the first reagent with the second reagent.

12. The method of claim 6, wherein the second time point is 4, 6, 8, 10, or 12 minutes upon mixing the first reagent with the second reagent.

13. The method of claim 1, comprising
    determining a first group of reaction rate changes at a first wavelength for a plurality of time points of a reaction period for mixing the first reagent with the second reagent,
    determining a second group of reaction rate changes at a second wavelength for said plurality of time points,
    wherein the first wavelength is within the absorbance wavelength region of the absorption spectrum for the metal nanoparticle or nanoshell and wherein the second wavelength is within a scattering wavelength region of the absorption spectrum for the metal nanoparticle or nanoshell,
    wherein an integration of the first group of reaction rate changes or an integration of the second group of reaction rate changes is indicative of the presence or absence of the complex of the first reagent and the second reagent.

14. The method of claim 13, wherein the integration of the first group of reaction rate changes is compared to a predetermined threshold value.

15. The method of claim 13, wherein the integration of the second group of reaction rate changes is compared to a predetermined threshold value.

16. The method of claim 13, wherein the first group of reaction rate changes are determined based on a first set of absorbance values corresponding to the first wavelength and a reference absorbance value corresponding to a reference wavelength, and wherein the second group of reaction rate changes are determined based on a second set of absorbance values corresponding to the second wavelength and the reference absorbance value.

17. The method of claim 16, wherein the reference wavelength is a wavelength corresponding to an isosbestic point.

18. The method of claim 13, wherein the first group of reaction rate changes are normalized based on an absorbance value of a control sample corresponding to the first wavelength and wherein the second group of reaction rate changes are normalized based on an absorbance value of the control sample corresponding to the second wavelength.

19. The method of claim 13, wherein the first group of reaction rate changes are normalized based on an absorbance value of a control sample corresponding to the first wavelength at a first time point in the reaction period and wherein the second group of reaction rate changes are normalized based on an absorbance value of the control sample corresponding to the second wavelength at the first time point in the reaction period.

20. The method of claim 13, wherein the first group of reaction rate changes are normalized based on an absorbance value corresponding to the first wavelength at a first time point in the reaction period and wherein the second group of reaction rate changes are normalized based on an absorbance value corresponding to the second wavelength at the first point in the reaction period.

21. The method of claim 1,
wherein the first reaction rate change is determined based on a first absorbance value corresponding to the first wavelength and a reference absorbance value corresponding to a reference wavelength,
wherein the second reaction rate change is determined based on a second absorbance value corresponding to the second wavelength and the reference absorbance value.

22. The method of claim 21, wherein the reference wavelength is a wavelength with minimum interference with absorbance or scattering of the first reagent, second reagent, and/or their complex.

23. The method of claim 21, wherein the reference wavelength is a wavelength corresponding to an isosbestic point.

24. The method of claim 4 or 6
wherein the first reaction rate change is determined based on a first absorbance value corresponding to the first wavelength and a reference absorbance value corresponding to a reference wavelength,
wherein the second reaction rate change is determined based on a second absorbance value corresponding to the second wavelength and the reference absorbance value,
wherein the third reaction rate change is determined based on a third absorbance value corresponding to the third wavelength and the reference absorbance value, and
wherein the fourth reaction rate change is determined based on a fourth absorbance value corresponding to the fourth wavelength and the reference absorbance value.

25. The method of claim 1, wherein the absorbance wavelength region is from about 280 nm to about 550 nm.

26. The method of claim 1, wherein the scattering wavelength region is from about 550 nm to about 800 nm.

27. The method of claim 1, wherein the first reagent is an analyte in a biological sample.

28. The method of claim 1, wherein the first reagent is an analyte in a biological sample and the second reagent is an entity that specifically binds to the first reagent.

29. The method of claim 1, wherein the first reagent is an analyte in a biological sample and the second reagent is an antibody that specifically binds to the first reagent.

30. The method of claim 1, wherein the first reagent is an analyte in a biological sample selected from the group consisting of epitopes of heartworm, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, and Group A *Streptococcus*.

31. The method of claim 1, wherein the second reagent is an antibody that specifically binds to an epitope of heartworm, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, or Group A *Streptococcus*.

32. The method of claim 1, wherein the metal nanoparticle or nanoshell is selected from the group consisting of gold particles, silver particles, copper particles, platinum particles, composite particles, gold hollow spheres, gold-coated silica nanoshells, and silica-coated gold shells.

33. The method of claim 1, wherein the first and second reaction rate changes are positive.

34. The method of claim 1, wherein the first and second reaction rate changes are negative.

35. The method of claim 1 further comprising determining the quantity of the complex of the first reagent and the second reagent based on the first reaction rate change and the second reaction rate change.

36. The method of claim 6 further comprising determining the quantity of the complex of the first reagent and the second reagent based on the first, second, third, and fourth reaction rate changes.

37. The method of claim 13 further comprising determining the quantity of the complex of the first reagent and the second reagent based on the first group of reaction rate changes and the second group of reaction rate changes.

* * * * *